(12) United States Patent
Uckun et al.

(10) Patent No.: US 6,953,875 B2
(45) Date of Patent: Oct. 11, 2005

(54) TRANSGENIC ZEBRA FISH EMBRYO MODEL FOR HEMATOPOIESIS AND LYMPHOPROLIFERATIVE DISORDERS

(75) Inventors: Fatih M. Uckun, White Bear Lake, MN (US); Alexcy O. Benyumov, Plymouth, MN (US)

(73) Assignee: Parker Hughes Institute, Roseville, MN (US)

( * ) Notice: Subject to any disclaimer, the term of this patent is extended or adjusted under 35 U.S.C. 154(b) by 43 days.

(21) Appl. No.: 10/144,926

(22) Filed: May 13, 2002

(65) Prior Publication Data

US 2003/0028909 A1 Feb. 6, 2003

Related U.S. Application Data

(63) Continuation of application No. PCT/US00/32757, filed on Nov. 30, 2000.
(60) Provisional application No. 60/168,110, filed on Nov. 30, 1999.

(51) Int. Cl.$^7$ ........................ A01K 67/00; A01K 67/27; A01K 67/033; C12N 15/00; G01N 31/00
(52) U.S. Cl. ............................ 800/10; 800/20; 800/25; 800/8; 800/3
(58) Field of Search .............................. 800/10, 20, 25, 800/8, 3

(56) References Cited

FOREIGN PATENT DOCUMENTS

WO      96 04372      2/1996

OTHER PUBLICATIONS

Kralovics, 2003, Clonal hematopoiesis in familial polycythemia vera suggests the involvement of multiple mutational events in the early pathogenesis of the disease, Blood, vol., 102, pp. 3793–3796.*
Cameron, 1997, Molec. Biotech. vol. 7, pp. 253–265.*
Wall, 1996, Theriogenology, vol. 45, pp. 57–68.*
Sheets, 1998, Nature Biotech., vol. 16, pp. 233–234.*
Kroll, 1996, Development, vol. 122, pp. 3173–3183.*
Long, 1997, Development, vol. 124, pp. 4105–4111.*
Miller–Bertoglio, 2000, Dissertation, The Johns Hopkins University, Chapter 3.*
Wood, 2000, Comparative Medicine, vol. 50, pp. 12–15.*
Houdebine, 1994, J. Biotech. vol. 34, pp. 269–287.*
Wang, 1997, PNAS, vol. 94, pp. 2386–2391.*
Overbeek, 1994, "Factors affecting transgenic animal production," Transgenic animal technology, pp. 96–98.*

Benyumov, Alexey O., et al: *Forced expression of the leukemogenic human Ikaros isoform 1k4 in transgenic zebra fish embryo during primitive hematopooiesis causes a lymphoproliferative disorder in adult fish*; BLOOD, vol. 94, No. 10 Suppl. 1 Part 1; Nov. 15, 1999, p. 467a XP000993361; Forty–first Annual Meeting of the American Society of Hematology; New Orleans, Louisiana, USA; Dec. 3–7, 1999; ISSN: 0006–4971.

Sun Lei, et al: "Expression of dominant–negative and mutant isoforms of the antileukemic transcription factor Ikaros in infant acute lymphoblastic leukemia"; Proceedings of the National Academy of Sciences of the United States, vol. 96, No. 2, Jan. 19, 1999, pp. 680–685, XP002166853 Jan. 19, 1999 ISSN: 0027–8424, figure 2.

L Sun, et al: "*Gene mutations and expression of dominant–negative IKAROS isoforms in T–cell acute lymphoblastic leukemia*"; Blood,US,W.B. Saunders, Philadelphia, VA, vol. 92, Nov. 15, 1998, p. 152A XP000864668; ISSN:0006–4971.

Al–Adhami et al., *Development Growth & Differentiation*, vol. 19, No. 2, pp. 171–179, 1977 Ontogenesis of Haematopoietic Sites in *Brachydanio rerio* (Hamiton–Buchanan) (Teleostei).

Amatruda et al., *Developmental Biology*, vol. 216, No. 1, pp. 1–15, 1999 Review: Dissecting Hematopoiesis and Disease Using the Zebrafish.

Amemiya et al., *Nature Genetics*, vol. 20, No. 3, pp. 222–223, 1998 The zebrafish and haematopoietic justice.

Bahary et al., *Stem Cells*, vol. 16, No. 2, pp. 89–98, 1998 Use of the Zebrafish (*Danio rerio*) to Define Hematopoiesis.

Brown et al., *Cell*, vol. 91, No. 6, pp. 845–854, 1997 Association of Transcriptionally Silent Genes with Ikaros Complexes at Centromeric Heterochromatin.

Brownlie et al., *Nature Genetics*, vol. 20, No. 3, pp. 244–250, 1998 Positional cloning of the zebrafish sauternes gene: a model for congenital sideroblastic anaemia.

Caldovic et al., *Molecular Marine Biology and Biotechnology*, vol. 4, No. 1, pp. 51–61, 1995 Development of position–independent expression vectors and their transfer into transgenic fish.

Crist et al., *Blood*, vol. 72, No. 6, pp. 1891–1897, 1988 Clinical Features and Outcome in Childhood T–Cell Leukemia–Lymphoma According to Stage of Thymocyte Differentiation: A Pediatric Oncology Group Study.

(Continued)

Primary Examiner—Joseph Woitach
Assistant Examiner—Valarie Bertoglio
(74) *Attorney, Agent, or Firm*—Merchant & Gould P.C.

(57) ABSTRACT

A transgenic zebrafish animal model is disclosed. The model can be used for study of hematopoetic cell differentiation, control, and screening of therapeutic agents and can include a transgenic zebrafish expressing a heterologous Ikaros protein.

17 Claims, 11 Drawing Sheets

OTHER PUBLICATIONS

Culp et al., *Proceedings of the National Academy of Sciences of the U.S.A.*, vol. 88, No. 18, pp. 7953–7957, 1991 High–frequency germ–line transmission of plasmic DNA sequences injected into fertilized zebrafish eggs.

Detrich et al., *Proceedings of the National Academy of Sciences of the U.S.A.*, vol. 92, No. 23, pp. 10713–10717, 1995 Intraembryonic hematopoietic cell migration during vertebrate development.

Ding et al., *Carcinogenesis*, vol. 10, No. 3, pp. 493–498, 1989 Differential susceptibility of a fish, Tilapia *Oreochromis mossambicus* (Teleostei, Cichlidae) to hepatocarcinogenesis by diethylnitrosamine and methylazoxymethanol acetate.

Driever et al., *The Journal of Clinical Investigation*, vol. 97, No. 8, pp. 1788–1794, 1996 The Zebrafish: Heritable Disorders in Transparent Embryos.

Earnest–Koons et al., *Journal of Wildlife Diseases*, vol. 33, No. 1, pp. 666–669, 1997 Lymphosarcoma in a Brook Trout.

Ford et al., *Nature*, vol. 363; No. 6427, pp. 358–360, 1993 In utero rearrangements in the trithorax–related oncogene in infant leukaemias.

Georgopoulos et al., *Science*, vol. 258, pp. 808–812, 1992 Ikaros, an Early Lymphoid–Specific Transcription Factor and a Putative Mediator for T Cell Commitment.

Georgopoulos et al., *Cell*, vol. 79, pp. 143–156, 1994 The Ikaros Gene Is Required for the Development of All Lymphoid Lineages.

Georgopoulos et al., *Annual Review of Immunology*, vol. 15, pp. 155–176, 1997 The Role of the Ikaros Gene in Lymphocyte Development and Homeostasis.

Gering et al., *The EMBO Journal*, vol. 17, No. 14, pp. 4029–4045, 1998 The SCL gene specifies haemangioblast development from early mesoderm.

Gill Super et al., *Blood*, vol. 83, No. 3, pp. 641–644, 1994 Clonal, Nonconstitutional Rearrangements of the MLL Gene in Infant Twins With Acute Lymphoblastic Leukemia: In Utero Chromosome Rearrangement of 11q23.

Greaves, M., *Science*, vol. 234, pp. 697–704, 1986 Differentiation–Linked Leukemogenesis in Lymphocytes.

Hahm et al., *Molecular and Cellular Biology*, vol. 14, No. 11, pp. 7111–7123, 1994 The Lymphoid Transcription Factor LyF–1 Is Encoded by Specific, Alternatively Spliced mRNAs Derived from he Ikaros Gene.

Haire et al., *Immunogenetics*, vol. 47, No. 4, pp. 336–337, 1998 Tec–family non–receptor tyrosine kinase expressed in zebrafish kidney.

Hammerschmidt et al., *Methods in Cell Biology*, vol. 59, pp. 87–115, 1999 Strategies to Perturb Zebrafish Development.

Hansen et al., *European Journal of Immunology*, vol. 27, No. 11, pp. 3049–3058, 1997 Conservation of a master hematopoietic switch gene during vertebrate evolution: isolation and characterization of Ikaros from teleost and amphibian species.

Hansen et al., *Immunological Reviews*, vol. 166, pp. 199–220, 1998 Lymphocyte development in fish and amphibians.

Hansen, J., *Immunogenetics*, vol. 46, No. 5, pp. 367–375, 1997 Characterization of rainbow trout terminal deoxynucleotidyl transferase structure and expression. TdT and RAG1 co–expression define the trout primary lymphoid tissues.

Hinton et al., *Fish Ecotoxicology*, Exs. 86, pp. 141–164, 1998 Architectural pattern, tissue and cellular morphology in livers of fishes: Relationship to experimentally–induced neoplastic responses.

Hyatt et al., *Methods in Cell Biology*, vol. 59, pp. 117–126, 1999 Vectors and Techniques for Ectopic Gene Expression in Zebrafish.

Ishikawa et al., *Cancer Research*, vol. 38, No. 11, pp. 3954–3959, 1978 Olfactory Neuroepithelioma in a Domestic Carp (*Cyprinus carpio*).

Jowett, T., *Methods in Cell Biology*, vol. 59, pp. 63–85, 1999 Analysis of Protein and Gene Expression.

Kent et al., *Leukemia*, vol. 11, Supp. 3, pp. 170–171, 1997 Plasmacytoid Leukemia of Chinook Salmon.

Klug et al., *Proceedings of the National Academy of Sciences of the U.S.A.*, vol. 95, No. 2, pp. 657–662, 1998 Hematopoietic stem cells and lymphoid progenitors express different Ikaros isoforms, and Ikaros is localized to heterochromatin in immature lymphocytes.

Lewbart et al., *The Veterinary Record*, vol. 143, No. 14, pp. 556–558, 1998 Surgical removal of an undifferentiated abdominal sarcoma from a koi carp (*Cyprinus cario*).

Liao et al., *Genes & Development*, vol. 12, No. 5, pp. 621–626, 1998 SCL/Tal–1 transcription factor acts downstream of cloche to specify hematopoietic and vascular progenitors in zebrafish.

Lieschke et al., *Blood*, Forty–First Annual Meeting (New Orleans, LA), pp. 651a, 1999 Marks an Anterolateral Site of Myeloid Commitment in the Postgastrulation Zebrafish Embryo Independent of Ventral Erythroid–Determining Signals.

Luna, Lee G., ed., *Manual of Histologic Staining Methods of the Armed Forces Institute of Pathology*, 3rd Ed., New York: McGraw Hill Book Company, 1968 Routine Staining Procedures: Method II Routine Harris Hematoxylin and Eosin Stain.

Meng et al., *Blood*, vol. 93, No. 2, pp. 500–508, 1999 Positive and Negative Cis–Acting Elements Are Required for Hematopoietic Expression of Zebrafish GATA–1.

Miller et al., *Immunological Reviews*, vol. 166, pp. 187–197, 1998 Functional and molecular characterization of teleost leukocytes.

Mizell et al., *The International Journal of Developmental Biology*, vol. 41, No. 2, 411–423, 1997 The aquatic vertebrate embryo as a sentinel for toxins: zebrafish embryo dechorionation and perivitelline space microinjection.

Molnar et al., *Molecular and Cellular Biology*, vol. 14, No. 12, pp. 8292–8303, 1994 The Ikaros Gene Encodes a Family of Functionally Diverse Zinc Finger DNA–Binding Proteins.

Molnar et al., *The Journal of Immunology*, vol. 156, No. 2, pp. 585–592, 1996 The Ikaros Gene Encodes a Family of Lymphocyte–Restricted Zinc Finger DNA Binding Proteins, Highly Conserved in Human and Mouse.

Morizot et al., *Molecular Carcinogenesis*, vol. 22, No. 3, pp. 150–157, 1998 Mapping of Tyrosine Kinase Gene Family Members in a Xiphophorus Melanoma Model.

Nguyen et al., *Developmental Biology*, vol. 199, No. 1, pp. 93–110, 1998 Ventral and Lateral Regions of the Zebrafish Gastrula, Including the Neural Crest Progenitors, Are Established by a bmp2b/swirl Pathway of Genes.

Nüsslein–Volhard, C., *Science*, vol. 266, pp. 572–574, 1994 Of Flies and Fishes.

Oberemm, A., *Lab Animal*, vol. 29, No. 7, pp. 32–39, 2000 The Use of a Refined Zebrafish Embryo Bioassay for the Assessment of Aquatic Toxicity.

Orkin et al., *Annual Review of Genetics*, vol. 31, pp. 33–60, 1997 Genetics of Erythropoiesis: Induced Mutations in Mice and Zebrafish.

Pliss et al., *Archiv Für Geschwulstforschung*, Band 52, No. 8, pp. 629–634, 1982 Peculiarities of N–nitramines carcinogenic action.

Poplack, D., ed., *Principles and Practice of Pediatric Oncology*, 2nd Ed., pp. 431–481 Acute Lymphoblastic Leukemia.

Ransom et al., *Development*, vol. 123, pp. 311–319, 1996 Characterization of zebrafish mutants with defects in embryonic hematopoiesis.

Rowley, A.F., ed., *Vertebrate Blood Cells*, By Rowley et al., New York: Cambridge University Press, 1988 Fish.

Schartl et al., *International Journal of Cancer*, vol. 36, No. 2, pp. 199–207, 1985 Elevated Expression of the Cellular SRC Gene in Tumors of Differing Etiologies in Xiphophorus.

Stainier et al., *Development*, vol. 121 (10), pp. 3141–3150, 1995 cloche, an early acting zebrafish gene, is required by both the endothelial and hematopoetic lineages.

Stuart et al., *Development*, vol. 109 (3), pp. 577–584, 1990 Stable lines of transgenic zebrafish exhibit reproducible patterns of transgene expression.

Sun et al., *Proc. Natl. Acad. Sci. USA*, vol. 96, pp. 680–685, 1999 Expression of dominant–negative and mutant isoforms of the antileukemic transcription factor Ikaros in infant acute lymphoblastic leukemia.

Sun et al., *The Embo Journal*, vol. 15, No. 19, pp. 5358–5369, 1996 Zinc finger–mediated protein interactions modulate Ikaros activity, a molecular control of lymphocyte development.

Thompson et al., *Developmental Biology*, vol. 197, No. 2, pp. 248–269, 1998 The cloche and spadetail Genes Differentially Affect Hematopoiesis and Vasculogenesis.

Trede et al., *Developmental & Comparative Immunology*, vol. 22, No. 3, pp. 253–263, 1998 Development of T–Cells During Fish Embryogenesis.

Uckun et al., *Blood*, vol. 91, No. 3, pp. 735–746, 1998 Biology and Treatment of Childhood T–Lineage Acute Lymphoblastic Leukemia.

Wang et al., *Immunity*, vol. 5, No. 6, pp. 537–549, 1996 Selective Defects in the Development of the Fetal and Adult Lymphoid System in Mice with an Ikaros Null Mutation.

Wang et al., *Nature Genetics*, vol. 20, No. 3, pp. 239–243, 1998 A zebrafish model for hepatoerythropoietic porphyria.

Weinstein et al., *Development*, vol. 123, pp. 303–309, 1996 Hematopoietic mutations in the zebrafish.

Westerfield, M., *The Zebrafish Book*, 4th Ed., Eugene, OR: University of Oregon Press, 2000 A guide for the laboratory use of zebrafish (*Danio rerio*).

Weston, K., *Oncogen*, vol. 18, No. 19, pp. 3034–3038, 1999 Reassessing the role of C–MYB in tumorigenesis.

Willett et al., *Developmental Dynamics*, vol. 214, pp. 323–336, 1999 Early Hematopoiesis and Developing Lymphoid Organs in the Zebrafish.

Willett et al., *Developmental Biology*, vol. 182, No. 2, pp. 331–341, 1997 Expression of Zebrafish rag Genes during Early Development Identifies the Thymus.

Winandy et al. *Cell*, vol. 83, No. 2, pp. 289–299, 1995 A Dominant Mutation in the Ikaros Gene Leads to Rapid Development of Leukemia and Lymphoma.

Wolff, L., *Critica Reviews™ in Oncogenesis*, vol. 7, Nos. 3&4, pp. 245–260, 1996 Myb–Induced Transformation.

Zhang et al., *Cell*, vol. 92, No. 2, pp. 241–251, 1998 Positional Cloning Identifies Zebrafish one–eyed pinhead as a Permissive EGF–Related Ligand Required during Gastrulation.

Zon, L., *Blood*, vol. 86, No. 8, pp. 2876–2891, 1995 Developmental Biology of Hematopoiesis.

* cited by examiner

FIG. 1A1
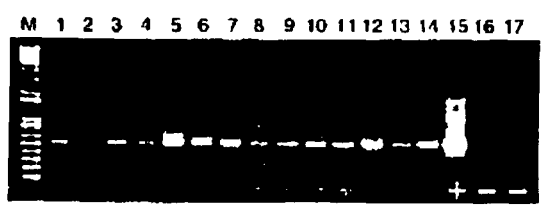
FIG. 1A2
FIG. 1A3
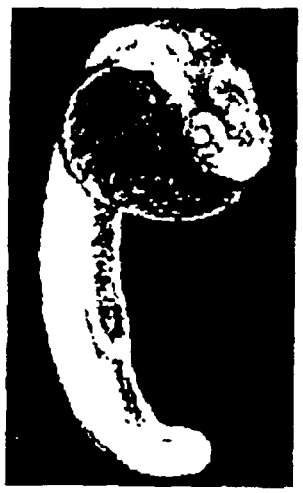
FIG. 1B1
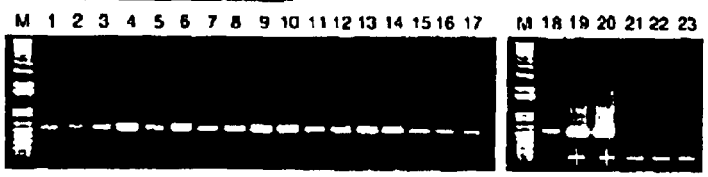
FIG. 1B2
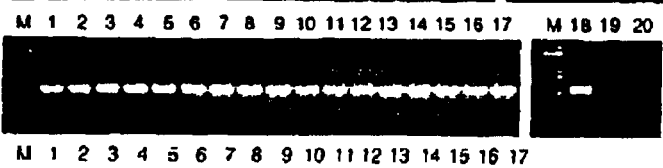
FIG. 1B3
FIG. 1B4

FIG. 1C1
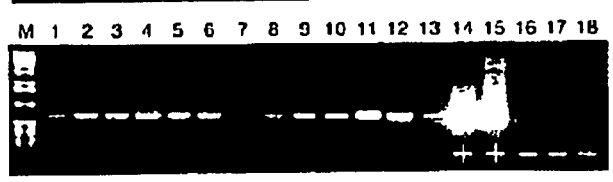
FIG. 1C2
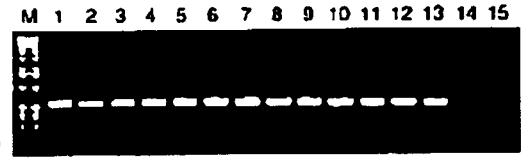
FIG. 1C3
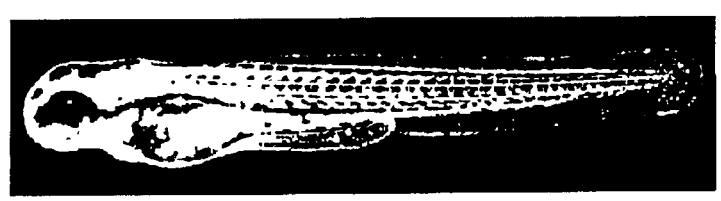
FIG. 1D1
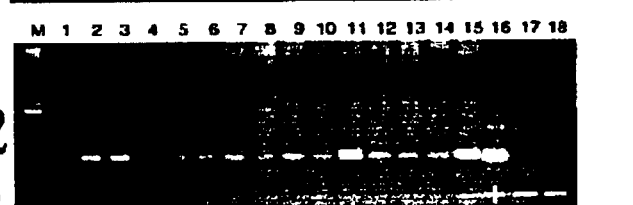
FIG. 1D2
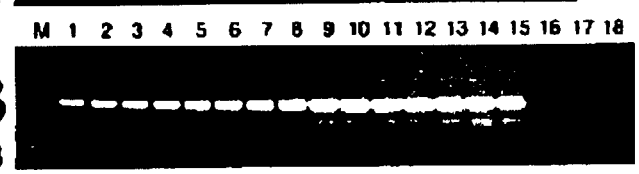
FIG. 1D3

FIG. 5C
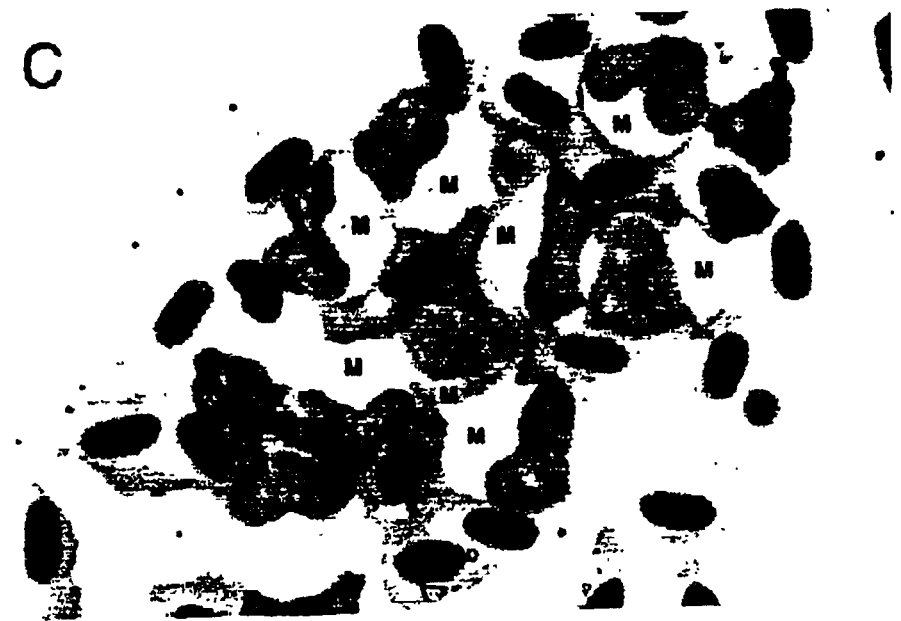
FIG. 5D

TRANSGENIC ZEBRA FISH EMBRYO MODEL FOR HEMATOPOIESIS AND LYMPHOPROLIFERATIVE DISORDERS

This application is a continuation of PCT/US00/32757, filed on Nov. 30, 2000, published in English on Jun. 7, 2001 as WO 01/40273, and designating the United States, which claims benefit of U.S. Provisional Application No. 60/168,110, filed on Nov. 30, 1999.

BACKGROUND OF THE INVENTION

Acute lymphoblastic leukemia (ALL) is the most common form of cancer in children (Pizzo and Poplack, 1993, Greaves, 1986, Uckun et al., 1998, Crist et al., 1988). A better understanding of the biological basis and predisposing leukemogenic events in this disease is needed in order to develop more effective treatment programs as well as novel prevention strategies.

Leukemic clones are thought to originate in ALL patients from normal lymphocyte precursors arrested at various stages of T- or B-lymphocyte development (Greaves, 1986). Accordingly, any critical regulatory network that controls normal lymphocyte development is a potential target for a leukemogenic event.

One such regulatory network vital for normal hematopoiesis involves Ikaros, a member of the Kruppel family "zinc finger" DNA-binding proteins. Ikaros acts as an evolutionarily conserved "master switch" of hematopoiesis that dictates the transcriptional regulation of lymphocyte ontogeny and differentiation (Georgopoulos et al., 1994, Georgopoulos et al., 1992, Hahm et al., 1994, Molnar and Georgopoulos, 1994, Wang et al., 1996, Winandy et al., 1995, Molnar et al., 1996, Sun et al., 1996, Hansen et al., 1997, Georgopoulos et al., 1997, Brown et al., 1997, Klug et al., 1998).

The programmed expression and function of the Ikaros gene is tightly controlled by alternative splicing of the Ikaros pre-mRNA which results in production of eight different Ikaros isoforms. All eight Ikaros isoforms share a common carboxy(C)-terminal domain containing a transcription activation motif and two zinc finger motifs that are required for hetero- and homodimerization among the Ikaros isoforms and for interactions with other proteins (Hahm et al., 1994, Molnar and Georgopoulos, 1994, Sun et al., 1996). Only three of the eight Ikaros isoforms, however, contain the requisite three or more amino(N)-terminal zinc fingers that confer high affinity binding to an Ikaros-specific core DNA sequence motif in the promoters of target genes (Sun et al., 1996).

The formation of homo- and heterodimers among the DNA binding isoforms increases their affinity for DNA, whereas heterodimers between the DNA binding isoforms and non-DNA binding isoforms are unable to bind DNA. Therefore, Ikaros proteins with fewer than three N-terminal zinc fingers exert a dominant negative effect by interfering with the activity of Ikaros isoforms that can bind DNA (Molnar et al., 1996, Sun et al., 1996). Thus, splicing errors can have severe consequences for the lymphocyte compartment of the developing immune system. An abundance of dominant-negative Ikaros isoforms that no longer bind DNA could result in significantly impaired expression of regulatory target genes that are essential for the orderly development and maturation of lymphocyte precursors.

In mice, absence of the normal Ikaros gene results in an early and complete arrest in the development of all lymphoid lineages during both fetal and adult hematopoiesis (Georgopoulos et al., 1994). Ikaros-deficient mice have a rudimentary thymus, lack peripheral lymph nodes, and are characterized by a complete absence of lymphocyte progenitor cells as well as mature B-lymphocytes, T-lymphocytes, and natural killer cells (Georgopoulos et al., 1994). Mice heterozygous for a germline mutation which results in the loss of critical DNA-binding zinc fingers of Ikaros develop a very aggressive form of lymphoblastic leukemia with a concomitant loss of the single wild type Ikaros allele between three and six months after birth (Winandy et al., 1995). Finally, the most recent findings in ALL molecular etiology show a pivotal role for Ikaros gene regulation in lymphoblast neoplastic transformation in infants (Sun et al., 1999) with T-lineage or B-lineage ALL leukemic cells expressing high levels of dominant-negative Ikaros isoforms.

It has long been suspected that molecular rearrangements in the lymphoid lineage precursors leading to ALL occur during fetal hematopoiesis (Ford et al., 1993, Gill Super et al., 1994). With the prospect of Ikaros malfunction and Ikaros isoform expression being at the core of leukemogenesis, a better understanding of the events taking place during embryonic blood cell differentiation is required in order to develop rational therapies. To address this need, an adequate experimental model system of vertebrate hematopoiesis is essential.

The zebrafish (ZF), with its extremely rapid embryonic development (3 days) and short maturation period (2–3 months) offers an attractive model. Over the past decade, the ZF embryo has been used to study eukaryotic gene activity and intercellular signaling in vertebrate development (Nusslein-Volhard, 1994, Zhang et al., 1998, Nguyen et al., 1998), and has emerged as a powerful genetic system, strongly relevant to the study of molecular medicine (Driever and Fishman, 1996, Amemiya, 1998). Intensive study of early embryonic hematopoiesis in the ZF along with the generation of hematopoietic mutants has turned the ZF into a useful model for the study of human blood disorders, such as congenital sideroblastic anemia (Brownlie et al., 1998) and hepatoerythropoietic porphyria (Wang et al., 1998). (See detailed reviews: Bahary and Zon, 1998, Amatruda and Zon, 1999).

It has now been discovered that transient, inappropriate expression during early embryonic development of the non-DNA binding Ikaros forms, including the dominant-negative isoforms, mutant forms, and others, have a significant impact on blood cell differentiation at later stages of development. Using the transgenic animal model of the invention, the effect of various agents on blood cell differentiation can be efficiently assessed. The ZF, with its relatively large and translucent embryo, external fertilization, and extracorporate development, provides a model of choice for transgenic research (Stuart et al., 1990, Culp et al., 1991, Hammerschmidt et al., 1999).

This model can be used, for example, to examine the impact of alteration of the Ikaros program of gene expression on definitive hematopoiesis in adults, within the short period of hematopoietic cell determination in ZF embryonic development.

As described herein, a transgenic Zebrafish (ZF) animal model provides an excellent model of vertebrate hematopoiesis.

SUMMARY OF THE INVENTION

The present invention provides a useful animal model for the screening and study of hematopoiesis and agents capable of modulating hematopoietic development. In particular, the ZF embryo carrying an Ikaros transgene provides a model for the study and modulation of lymphocyte development and leukemia.

In one embodiment of the invention, the transgene is a DNA-binding Ikaros isoform, for example, Ik-2. The ZF embryo animal model carrying the Ik-2 transgene can be used to screen and identify agents that interfere with or overcome normal Ik-2 function, for example, inducing B- or T-cell cancers, particularly leukemia. Potential cancer-inducing agents such as proteins, gene alterations, pharmaceuticals, toxins, and the like, are screened by administration to the model, and the disruption of normal function is monitored. An Ik-2 transgenic ZF embryo model thus can provide a screening assay for potential carcinogens.

In an alternative embodiment of the invention, the ZF embryo is transformed with a non-DNA binding form of Ikaros. The non-DNA binding form can be, for example, Ik-4, 5, 6, 7, 8, 9, or 10, each of which lacks the three N-terminal zinc fingers required to confer high affinity DNA binding. A mutant Ikaros protein can also be used, for example those Ik deletion and insertion mutants described in PCT Patent Application PCT/US99/26274 and discussed more fully below. Because the ZF model containing a non-DNA binding Ik, e.g. Ik-4, develops leukemia at later stages of development, it can be used to screen for preventative and therapeutic agents.

BRIEF DESCRIPTION OF THE FIGURES

FIGS. 1A1–1D3 are computer generated images demonstrating successful microinjection and expression of human Ikaros proteins in Zebrafish embryos.

FIGS. 1A2, and 1A3 show a gfp-positive ZF embryo at mid gastrula stage, 6 hpf (FIG. 1A1), and Ikaros CDNA (FIG. 1A2) and control beta actin CDNA (FIG. 1A3) amplified from embryonic mRNA.

FIGS. 1B1–1B4 show a gfp-positive ZF embryo at prim-5 stage, 24 hpf (FIG. 1B1), and Ikaros EDNA (FIG. 1B2) and control beta actin cDNA (FIGS. 1B3, 1B4) amplified from embryonic mRNA.

FIGS. 1C1–1C3 show a gfp-positive ZF embryo at prim-5 stage, 24 hpf (FIG. 1C1), and Ikaros cDNA (FIG. 1C2) and control beta actin CDNA (FIG. 1C3) amplified from embryonic mRNA.

FIGS. 1D1–1D3 show a gfp-positive ZF embryo at long-pec stage, 48 hpf (FIG. 1D1), and Ikaros cDNA (FIG. 1D2) and control beta actin cDNA (FIG. 1D3) amplified from embryonic mRNA.

FIG. 2A shows a control embryo at 17 hpf with a negative hybridization result using the Ik-4 rhyboprobe.

FIGS. 2B–2D show Ik-4 injected embryos at 17 hpf, each demonstrating positive hybridization result with Ik-4 expression in the trunk region of the embryo. FIGS. 2E–2F are Ik-2 injected embryos at approximately 17 hpf, demonstrating positive hybridization with Ik-2 expression in the trunk region of the embryo.

FIG. 3B demonstrates Ik-4 immunostaining localized to the nuclei and cytoplasm in circulating blood cells, while FIG. 3C demonstrates Ik-4 immunostaining in the mesenchymal hematopoictic cells of the dorsal aorta ventral wall.

FIG. 3D demonstrates Ik-2 immunostaining localized to the nuclei and cytoplasm of cirulating blood cells. Specificity of the anti-Ikaros antibodies to the human protein was confirmed by control staining. In non-injected ZF embryos, no cross reactivity with the endogenous ZF Ikaros was observed (FIG. 3E).

FIG. 4A is a control embryo at 17 hpf with GATA-1 positive cells in the trunk region stained pink with fast red. No Ikaros staining is present.

FIG. 4O shows an Ik-2 injected ZF larvae at 5 dpf without lck positive thymic site.

FIGS. 5B–5C are computerized microscopic images of kidney hematopoietic cells imprinted onto slides from intact embryos and differentially stained with Wright/Giesma.

FIG. 5B shows imprinted cells of ZF kidney derived from Ik-2 injected embryos.

FIG. 5D shows kidney hematopoietic cells from ZF derived from Ik-4 injected embyos.

In FIGS. 5B, 5C, and 5D myeloid cells are marked as M, erythroblast cells are marked as E, and lymphoid cells are marked with arrows pointing to the cells.

DETAILED DESCRIPTION OF THE INVENTION

Figure 2A:
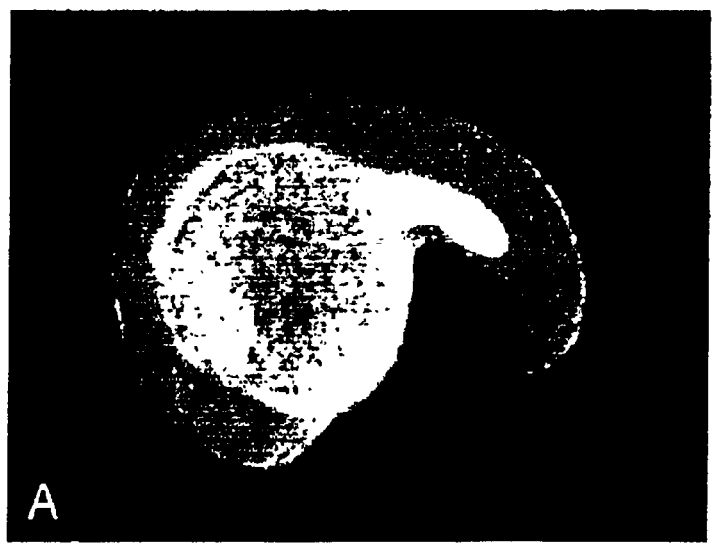
FIGS. 2A–2F are computerized photographic images demonstrating Ik-4 and Ik-2 transgene expression in ZF embryos by whole-mount in situ hybridization.
Figure 2B:
Figure 2C:
Figure 2D:
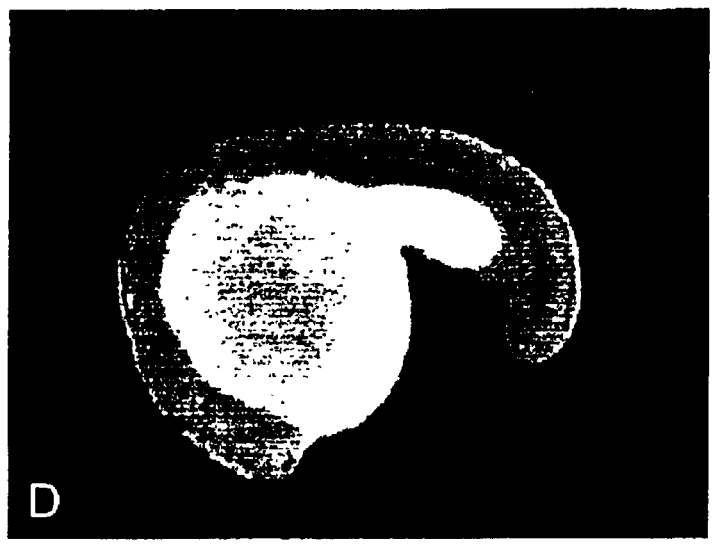
Figure 2E:
Figure 2F:
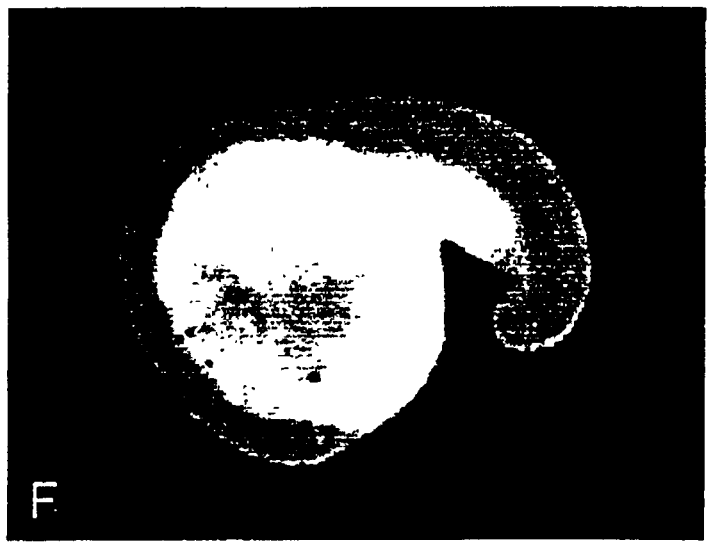

The instant invention relates to the discovery that expression of Ikaros isoforms in ZF embryos provides modulation of hematopoietic cell development. Such modification is specific, and correlates with development events in human hematopoietic cells and with specific hematopoietic disorders, including leukemias and anemias.

Accordingly, the transgenic ZF animal model described more fully in the examples below provides a rapid and efficient screening assay for agents that modulate normal hematopoietic cell development. The animal model is thus useful for studying and understanding regulation of hematopoietic, as well as for screening agents for prevention and/or therapeutic applications.

In a preferred method of the invention, a zebrafish embryo carrying a transgene encoding a DNA-binding or non-DNA binding Ikaros protein is provided for analysis. ZF embryos expressing DNA binding Ikaros protein are useful for studying normal B- and T-cell lineage development, and for screening agents suspected of altering normal development. In addition, this model can be used to screen agents effective to increase red blood cell counts, as an indication of useful anti-anemia therapy.

ZF embryos expressing non-DNA binding isoforms (Ik-4, 5, 6, 7, 8 and deletion or insertion Ik mutants) can be used to screen for potential therapeutic candidates, particularly for the prevention and/or treatment of hematopoietic disease. Examples of mutant Ikaros proteins include those lacking the following amino acid sequence: KSSMPQKFLG [SEQ ID NO: 5]. An exemplary insertion mutant is an Ikaros protein containing an insertion of the following amino acid sequence: VTVGADDFRDFHAIIPKSFSR [SEQ ID NO 6]

EXAMPLES

The invention may be better understood with reference to the following Examples. These are intended only to exemplify the invention, and not to limit the scope of the invention in any way.

Example 1

Expression Constructs and Microinjection of Zebrafish Embryos

Fish and embryos. The adult wild type ZF were maintained generally according to the Zebrafish book recommendations (Westerfield, 1995).

Males and females were kept in 10 G tanks, 70 fish per tank, with a constant slow flow of conditioned water at 26° C. and a controlled 14 hours day/10 hours night cycle. Embryos were obtained through natural spawning in breeding cages with a netted false bottom or by in vitro fertilization using eggs and milt collected from the mature females and males anesthetized with tricaine (Sigma). Embryos were kept at 28.5° C. in Petry dishes, 30–50 per dish.

Five days after hatching, frys were transferred to a nursery for 2 weeks and raised in 1 G mouse cages at 28.5° C. Larvae were fed with live food, paramecia and brine shrimps, according to recommendations of Dr. Stephen Ekker (personal communication). The survival rate was over 95%. Juvenile ZF were transferred to 10 G tanks, treated as adult fish as described above and raised to maturity for another 3 months. For in situ hybridization studies, embryos at 1–5 days post fertilization (dpf) were treated with 0.003% phenylthiourea (Sigma) to prevent pigmentation.

Genes and expression vectors. Transgenic expression of human Ikaros isoforms Ik-2 and Ik-4 were driven by the promoter/enhancer region of carp β-actin gene in all-fish expression vector pFV4aCAT (Caldovic and Hackett, 1995). The DNA vectors were constructed by cloning the human wild type Ikaros cDNA Ik-2 and Ik-4 into pFV4aCAT at the NotI and SpeI sites. The vectors were re-named hIK4wt pFV4aCAT and hIK2wt pFV4aCAT, respectively. After further digestion with XbaI, the linearized fragments containing Ikaros cDNA were then purified with a Spin X column (Costar) and used for microinjections.

Microinjections. Microinjections were performed with the help of a SMZ-10A stereo microscope (Nicon) and Transjector 5246 (Eppendorf) at room temperature (RT) using glass micropipettes with splinted sharp tips of 2–3 μm diameter. The eggs in chorions at the early one-cell stage were positioned in grooves of agar-lined Petri dishes, as described in Westerfield, 1995.

The constructs were coinjected, according to the method recommended by Hyatt and Ekker, 1999, with green fluorescent protein (GFP) mRNA (147.4 ng/μL), to confirm the presence of the injected molecules and to enable selection of GFP-positive fish for future analyses. DNA was dissolved to a final concentration of 10 ng/μL in Hank's saline containing 0.01% phenol red, in order to follow the injection procedure. Approximately 5 nl of the injected medium containing the equivalent of approximately 50 pg ($10^7$ copies) of the construct was injected into the cytoplasm of the egg's blastodisk under visual control. Each construct was injected independently in 3–5 series of injections and the data obtained was pooled. Following the injections, eggs were incubated at 28.5° C.

Embryo observations were carried out with a SMZ-10A stereo microscope (Nicon), equipped with an additional filter setting for fluorescence detection and a specially designed transparent heating tray to keep embryos at constant temperature. Pictures of the embryos were taken with a H-III Photomicrographic System (Nicon) on Ektachrome 100X film (Kodak). Fluorescent embryos were imaged using MRC-1024 Laser Scanning Confocal Imaging System (Bio-Rad). The embryos and larvae were observed and analyzed at 6, 24, and 48 hours post fertilization (hpf) and at 3, 4, and 5 days post fertilization (dpf), or were raised to adulthood for future analyses (see above).

mRNA Isolation and RT-PCR. mRNA was extracted from individual zebrafish embryos and adult fish tissues using the Oligotex™Direct mRNA isolation Kit (Qiagen, Valencia, Calif.). Possible DNA contamination was eliminated by incubating all mRNA with 1 μl DNase (Promega, RQ1 RNase Free DNase) in 100 μl final volume of buffer containing 50 mM NaCl, 5 mM Tris-Cl, pH7.5 at 37° C. for 30 minutes. The reactions were stopped by phenol/chloroform extraction and mRNA was precipitated with ethanol. Reverse transcription was done with a 500 ng mRNA template in the 20 μl final volume using Advantage™ RT-for-PCR Kit (Clontech). The CDNA obtained by reverse transcription was diluted to a total volume of 100 μl by adding 80 μl H₂O. PCR amplification of Ikaros CDNA was achieved using 10 μl of the diluted cDNA as template and the Advantage® cDNA Polymerase Mix (Clontech) in a 50 μl reaction volume. Primers for amplification of Ikaros CDNA are shown below:

F1, 5'-ATGGATGCTGACGAGGGTCAAGAC-3'   [SEQ ID NO: 1]
and
R1, 5'-CTAGTGGAATGTGTGCTCCCCTCG-3'.   [SEQ ID NO: 2]

The integrity of the mRNA and CDNA was confirmed by PCR amplification of zebrafish β-actin CDNA in the same reaction with primers specific for β-actin:

ACTf, 5'-GATGATGCCCCTCGTGCTGTTTTC-3' [SEQ ID NO: 3]
and
ACTr, 5'-TTTCTCTTTCGGCTGTGGTGGTGA-3'. [SEQ ID NO: 4]

The 4 kb injected DNA fragment was used as a positive control PCR template for comparison to the size of the amplified fragments.

Sectioning. Dechorionated or hatched ZF embryos at 48 hpf were fixed in 4% paraformaldehyde/phosphate buffer (PBS) at 4° C. for 2 hours, soaked in 30% sucrose, embedded into OCT cryostat embedding medium (Fisher) and frozen in liquid $N_2$ exactly as described previously in Westerfield, 1995. Sections of 5 µm were prepared with the cryotome CM 1800 (Lieca). Slides with mounted ZF sections were stored at −80° C. until rehydrated by washing 3 times with PBS, pH 7.4 (Celox Laboratories). Sections were stained with hematoxyline and eosine as described in Luna, 1968, or subjected to immunostaining.

Immunostaining. Tissue sections were permeabilized by soaking with a blocking solution of PBS containing 2.5% bovine serum albumin (BSA) (Sigma) and 0.1% Triton-X-100 (Fisher Biotech) for 30 minutes, and then treated with primary antibodies (rabbit anti-Ikaros IgG (1:100), Parker Hughes Institute) for 1 hour at room temperature. Treated sections were washed 3 times with PBS, stained with fluorescein isothiocyanate-labeled secondary antibodies (donkey anti-rabbit Ig (1:40), Amersham) for 1 hour at room temperature and washed 3 times with PBS, after which Vectashield mounting medium with propidium iodide (Vector Laboratories) and coverslips were applied. Stained ZF embryo sections were imaged using MRC-1024 Laser Scanning Confocal Imaging System (Bio-Rad).

Whole-mount in situ hybridizations were carried out on embryos at 15–19 hpf and 4, 5 dpf according to the methods described in Jowett, 1999. Ikaros riboprobes were labeled with digoxigenin, whereas GATA-1, c-MYB, Rag-1, and lck probes, used in two-color/fluorescent iii situ hybridizations, were labeled with fluorescein. Synthesis of RNA probes was performed by in vitro transcription using a DIG RNA Labeling Kit (Roche Molecular Biochemicals). For Ikaros riboprobes, human Ikaros cDNA (Ik-4 or Ik-2) used as a template was cloned to the pBluescript/KS+ vector and linearized at the XhoI site. Anti-sense RNA was in vitro transcribed with T7 RNA polymerase for 2 hours at 37° C. and labeled by digoxigenin-11-UTP added to the nucleotide mixture. GATA-1 template cloned to the pBlueskript/SK+ vector was linearized with XbaI. c-MYB or lck cloned to pBKCMV were linearized with EcoRI, and Rag 1 cloned to pCR 2.1 vector was linearized with Hind III restriction endonuclease.

Anti-sense probes were synthesized with T7 RNA polymerase, as above. Sense probes used for control staining were synthesized with T3 RNA polymerase. Prior to in situ hybridization, the efficacy of reaction was confirmed by gel electrophoresis and Northern hybridization. Embryos fixed with 4% paraformaldehyde for 12 hours at 4° C. were gradually dehydrated in methanol and kept at −20° C. overnight. Following rehydration, embryos were prehybridized for 5 hours at 70° C., then hybridized with corresponding riboprobe(s) at 70° C. (overnight) and finally treated with anti-DIG or anti-fluorescein Fab fragments for immunolocalization of the haptens. Detection of the DIG antibody-alkaline phosphatase conjugate was carried out by staining with nitroblue tetrazoleum/5-bromo-4-chloro-3-indolilphosphate (NBT/BCIP) substrate mixture which produces an insoluble, blue-purple precipitate. Visualization of fluorescein antibodies conjugated to alkaline phosphatase complex was accomplished by staining with Fast Red (Boehringer Mannheim) which produces a precipitate that is both chromogenic (pink) and fluorescent. After hybridization, embryos were re-fixed in 4% paraformaldehyde and photographed. Images of embryos were then taken with an H-III Photomicrographic System (Nicon) on Ektachrome 100X film (Kodak). Fluorescence in the embryos was detected and imaged using MRC-1024 Laser Scanning Confocal Imaging System (Bio-Rad) mounted on a Nikon Eclipse ESOO upright microscope with high numerical aperture objectives. Digital data from 30–34 optical section series were collected and 3D images were reconstructed using Lasersharp software (Bio-Rad, Hercules Calif.) and printed on a Fuji Pictrography thermal transfer printer (Fuji, Elmsford, N.Y.).

Adult fish, tissues, and kidney imprints. The size, color, sex and weight of adult three-month-old fish were determined. Blood was collected from the caudal vein from anesthetized fish and organs/tissues (spleens, intestines, brains, eyes, hearts, and kidneys) were dissected and frozen in liquid Nitrogen for RT-PCR analysis. Prior to freezing, color and weight of spleens and livers were analyzed and weight indexes were calculated (weight of the organ×100/total fish weight). Kidneys were imprinted on slides which were air dried and stained with Wright/Giemsa according to the University of Maryland Special Hematology Laboratory protocols. Kidney imprints were studied microscopically for cellular composition and photographed using a microscope Eclipse E800 (Nicon) and a H-III Photomicrographic System (Nicon).

Cell morphology analysis. Blood cells were typed according to cell morphology and PAS, Sudan black, and myeloperoxidase staining. Cell counts in the kidney imprints were performed at ×100 magnification using an eye-piece grid in 10 different areas of each sample. The number of lymphoid, myeloid, and erythroid cells as well as granulocytes and monocytes was determined and cell indexes were calculated for each of the cell lineages.

Statistics. Data obtained from adult fish measurements and from kidney cell counts were checked for normal distribution and subjected to a standard Student's two-tailed test with Welch's correction, when necessary. Statistical analysis and graphing were performed using GraphPad Prism version 2.0 (GraphPad Software, Inc., San Diego, Calif.).

Example 2

Transgenic Expression of Human Ikaros Isoforms Ik-4 and Ik-2 in ZF Embryos

Linearized expression vectors hIK4 wt pFV4aCAT and hIK2 wt pFV4aCAT were mixed with GFP mRNA and microinjected into one-cell stage ZF embryos to force expression of the dominant-negative human Ikaros isoform Ik-4 and the DNA binding human Ikaros isoform Ik-2 (control) during primitive hematopoiesis. The microinjections were successful in >95% of all embryos, as evidenced by a strong green fluorescence documenting the expression of the coinjected GFP mRNA from mid-gastrula until prim-5 stage (FIGS. 1A1, 2A1,3A1).

Total mRNA was extracted from GFP-positive individual ZF embryos at 6 hpf, mid-gastrula stage (FIG. 1A1), at 24 hpf, prim-5 stage (FIGS. 1B1, 1C1) and at 48 hpf, Long-pec stage (FIG. 1D1). The extracted mRNA was reverse-transcribed using oligo-dT and random hexamers. The resulting cDNAs were amplified with ZF β-actin primers (FIGS. 1A3, 1B3, 1C3, and 1D3) to test the integrity of the extracted mRNAs. Human Ikaros expression was analyzed by amplification with Ikaros-specific primers hIKEX7R1 and hIKEXIF (FIGS. 1A2, 1B2, 1C2, and 1D2).

RT-PCR analysis of total RNA from GFP-positive embryos (n=13–18 per time point) confirmed the time-dependent expression of human Ik-4 and Ik-2 mRNA. At late blastula stage (4 hpf), no human Ikaros transgene expression had been detected, likely due to a lack of transcriptional activity of the zygotic genes (data not shown). In contrast, during embryonic shield formation at mid-gastrula stage (6 hpf), prim-5 stage (24 hpf), and long-pec stage (48 hpf), 100% of the tested embryos expressed the corresponding human Ikaros transgene (1A2, 1B2, and 1C2, respectively).

Expression of the human Ikaros transgenes Ik-4 and Ik-2 was transient. Only half of the hatching embryos (72 hpf), one third of the larvae (96 hpf), and none of the adult ZF tissues showed RT-PCR evidence for human Ikaros trans-gene expression (data not shown). Microinjections did not significantly affect the viability and survival rate of the ZF embryos. Of 162 non-injected control embryos, 146 (90.1%) developed up to hatching without any visual abnormalities. Similarly 316 of 361 (87.5%) GFP-positive embryos micro-injected with the Ik-4 expression vector hIk4wt pFV4aCAT and 256 of 303 (84.5%) GFP-positive embryos microinjected with the Ik-2 expression vector hIk2wt pFV4aCAT developed normally (Table 1).

TABLE 1

Survial Rates and Embryonic Development following Ikaros injections

| Construct | # Injected Fertilized Eggs (n) | # GFP-Positive Embryos at 3–6 hpf | # Normal Embryos 3–48 hpf* n (%) | # Normal Larval 72–96 hpf (n) | # Oligo-chromen Larval 72–96 hpf n (%) |
|---|---|---|---|---|---|
| Ik4 | 379 | 361 | 316 (87.5%) | 183 | 27 (13%) |
| Ik2wt | 312 | 303 | 256 (84.5%) | 235 | 11 (4.5%) |
| act control | 162 | 0 | 146 (90.1%) | 134 | 5 (3.7%) |

*including embryos taken for analysis

A lack of pigmentation (a/oligochromemia) in the circulating blood cells as seen through pericardium, was observed at 48–72 hpf in 27 out of 183 (13%) Ik-4 injected embryos and fry. This data is contrasted with a/oligochromenia observed in only 4.5% and 3.7% of the Ik-2 injected embryos and intact control, respectively.

Example 3 in situ Localization of nIkaros Transgenes

The topographical profile of the human Ikaros transgenes Ik-4 and Ik-2 expressed in the ZF embryos at 17–19 hpf was confirmed by whole-mount in situ hybridization using digoxigenin-labeled Ikaros riboprobes. Probes hybridized to the human Ikaros mRNA were immunolocalized with anti-DIG Fab fragments and detected by chromogenic reaction with NBTIBCIP. No false positive signals were detected in non-transgenic control ZF embryos (FIG. 2A). In transgenic ZF embryos, the chromogenic (blue-purple) signal of human Ik-4 or Ik-2 transgene expression was largely localized to the trunk region containing the intermediate cell mass (ICM) where primitive hematopoiesis takes place (FIGS. 2B-2F), reminiscent of the expression profile of other regulators of hematopoiesis such as GATA-1 and c-MYB (Detrich et al., 1995, Amatruda and Zon, 1999).

Figure 3A:
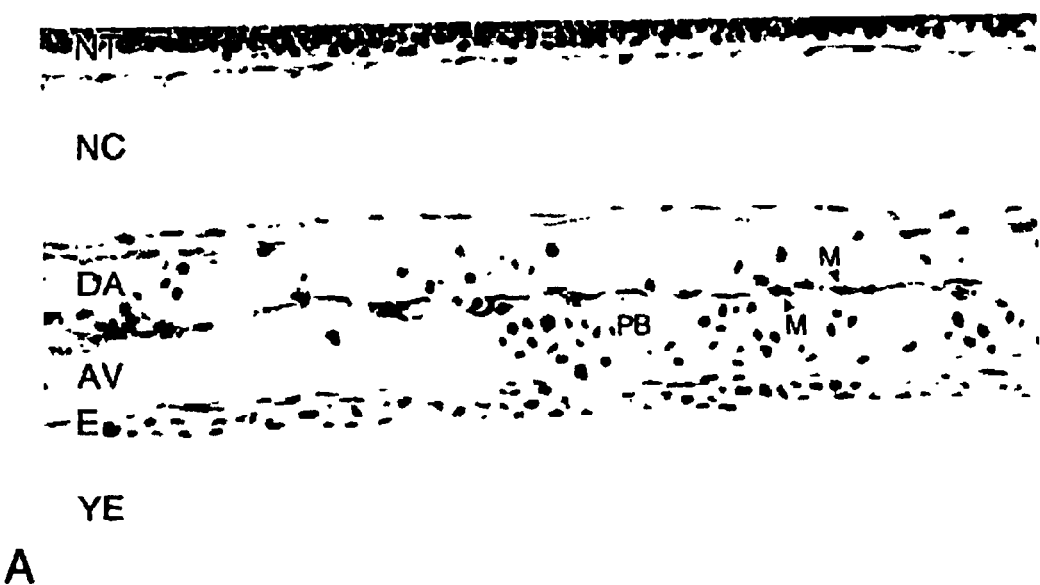
FIG. 3A is a computerized photograph of a medium sagittal section of the trunk region of a 48 hpf ZF embryo showing anterior to the left and dorsal to the top of the frame and providing a layout of the "dorsal" hematopoietic site.

At 48 hpf, embryonic hematopoiesis in the ZF shifts from the ICM to the dorsal mesentery and forms the "dorsal" fetal hematopoietic site (Detrich et al., 1995, Amatruda and Zon, 1999). At this transition stage from primitive to definitive hematopoiesis, the trunk axial vessel complex, i.e., dorsal aorta and axial vein, stretches along the anterior-posterior axis, between the notochord and trunk endoderm, and contains circulating embryonic blood cells (FIG. 3A). ZF embryos derived from the Ik-4 injected and from the Ik-2 injected eggs were fixed with paraformaldehyde at 48 hpf and frozen sagittal section were stained with hematoxylin/eosin or immunostained with the antibodies raised against human Ikaros. Sections were examined by laser confocal microscopy. The median saggital section of the trunk region (A) of the 48 hpf ZF embryo with anterior to the left and dorsal to the top of the frame, provides a layout of the "dorsal" hematopoietic site with dorsal aorta (DA) and axial vein (AV) with mesenchyme hematopoietic cells of the dorsal aorta ventral wall (M) and circulating primitive blood cells (PB). From the dorsal side the axial major vessel complex are bordered by the notochord (NC) and neural tube (NT); from the ventral side the vessels are neighbored by the endoderm (E) and the yolk extension (YE).

Examination of the sagittal sections of the trunk region in Ikaros tranagenic ZF embryos by immunofluorescence staining with antibodies directed against human Ikaros and confocal laser scanning microscopy showed expression of human Ikaros in circulating lymphohematopoietic cells (FIG. 3B) as well as in the cells of the ventral wall of dorsal aorta (FIG. 3C) and ventral vein region (data not shown). Human Ik-4 isofonn showed cytoplasmic and patchy nuclear expression in hemaropoictic cells of transgenic ZF embryos (FIGS. 3B–3C), reminiscent of its intracellular localization pattern in human cells (Sun et al., 1999). A similar pattern of subcellular compartmentalization was observed in circulating ZF blood cells expressing the Ik-2 isoform. Ik-2 protein was detected in the nuclei and cytoplasm of the blood cells (FIG. 3D). No false positive signals were detected in non-transgenic control ZF embryos (FIG. 3E).

Example 4

Deregulated Expression of GATA-1, c-MYB and lck Genes in Human Ik-4 and Ik-2 Transgenic ZF Embryos The impact of Ik-4 and Ik-2 transgene expression in the ZF embryos on the expression pattern of the early hematopoietic and lymphopoietic markers GATA-1, c-MYB, Rag-1, and lck was evaluated. Ik-4 and Ik-2 transgene expression interferes with the normal expression of ZF GATA-1, c-MYB, and lck, but not with Rag-1. The zinc-finger transcription factor GATA-1 is one of the central regulators in hematopoietic cell differentiation within the myeloid and erythroid lineages (as thoroughly reviewed by Orkin and Zon, 1997). The transcriptional regulator of myelopoiesis encoded by the proto-oncogene c-MYB and its target c-myc have been implicated in myeloid leukemogenesis, as reviewed by Wolff, 1996 and Weston, 1999. Both GATA-1 and c-MYB are expressed in the ZF during 15–24 hpf and they strongly demarcate the forming ICM, the earliest site of primitive hematopoiesis (Detrich et al., 1995, Liao et al., 1998, Bahary and Zon, 1998).

By comparison, expression of the lymphoid marker Rag-1 in the ZF commences at 3 dpf, when thymocyte precursors seed the bi-lateral thymic anlage (Trede and Zon, 1998). A similar pattern of expression restricted to bilateral thymi was shown for lck (Dr. Nikolaus Trede, personal communication).

Expression patterns of the ZF early hematopoietic genes in the presence of Ik-4 and Ik-2 transgene expression were studied in the ZF embryos by means of two color/fluorescence whole-mount in situ hybridization. All images are positioned anterior to the top and dorsal side to the right of the frame.

In contrast to the first two markers, Rag-1 expression is restricted to thymocytes after they seed the thymus anlagae at 3 dpf. We observed Rag-1 expression in the bi-lateral thymi at 4 dpf in all tested fish from the Ik-4 injected and Ik-2 injected groups and in the control with no regard to the transgene expression. Rag-1 was transcribed bi-laterally in the location of thymus primordial.

Figure 4A:
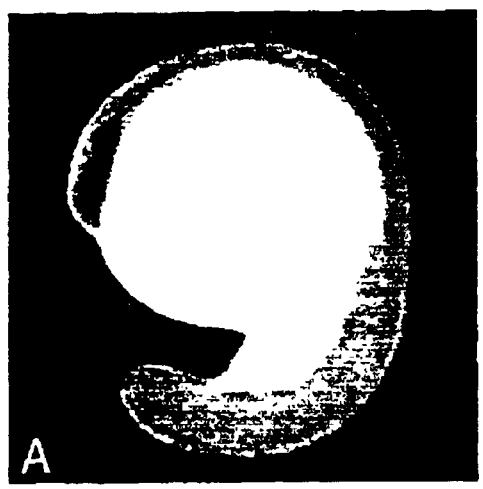
FIGS. 4A–4O are computerized photographic images showing expression patterns of the ZF early hematopoietic genes GATA-1, c-MYB, Rag-1, and lck.
Figure 4B:
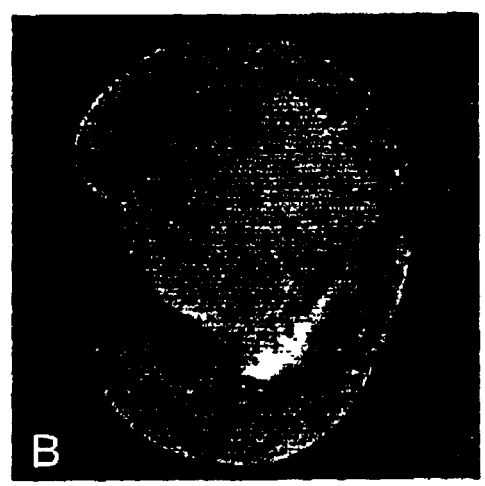
FIG. 4B is a lateral view of an Ik-4 transgenic embryo at 17 hpf showing blue-purple spots in patches marking Ik-4 expression and a strong pink staining of the ICM region.
Figure 4C:
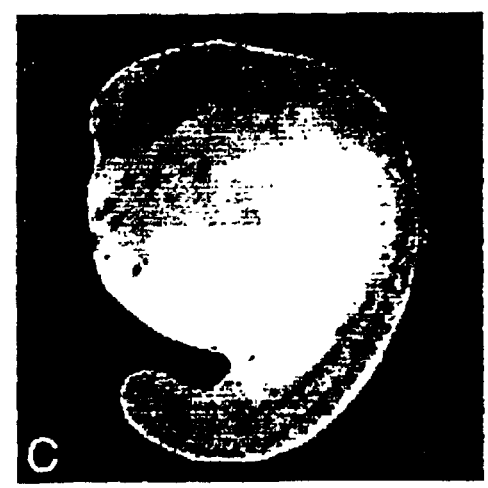
FIG. 4C is a lateral view of an Ik-2 transgenic embryo at 17 hpf showing blue-purple signals of the Ik-2 and no traces of GATA-1 expression.
Figure 4D:
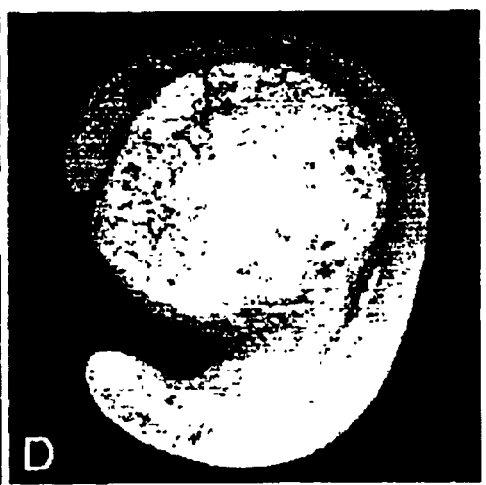
FIG. 4D is a laser confocal image of the embryo shown in FIG. 4A, with fluorescent GATA-1 positive ICM staining.
Figure 4E:
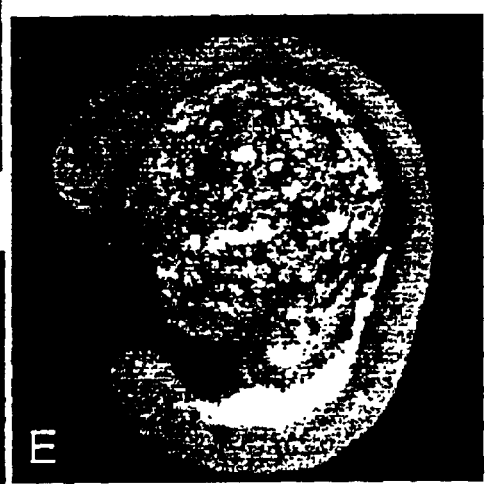
FIG. 4E is a laser confocal image of the embryo shown in FIG. 4B, having a dramatic increase in the ICM due to abnormal expansion of GATA-1 positive cells.
Figure 4F:
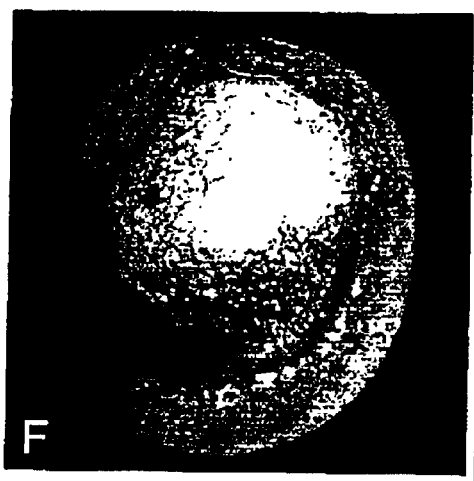
FIG. 4F is a laser confocal image of the embryo shown in FIG. 4C, demonstrating a decline in GATA-1 expression.

Following two color/fluorescence in situ hybridization with human Ikaros and ZF GATA-1 riboprobes, all non-injected control embryos at 17 hpf were found positive for GATA-1 expression and showed no false positive signals of human Ikaros expression (FIG. 4A). GATA-1 positive cells formed a distinct strip of the ICM in the trunk region between the somite mesoderm and the yolk protrusion, which was remarkably vivid with the use of fluorescence (FIG. 4D). Notably, in the ZF embryos expressing the human Ik-4 transgene, the GATA-1 positive ICM region was much larger than in non-injected control embryos (FIGS. 4B & 4E). In contrast, in the ZF embryos expressing the Ik-2 transgene, the GATA-1 positive cells in the ICM site were few and formed a dotted rather than a solid line (FIGS. 4C & 4F).

Figure 4I:
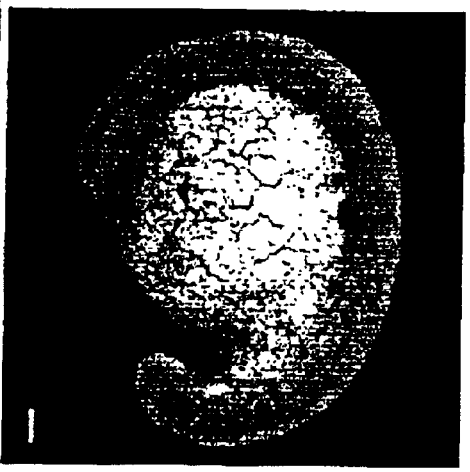
FIG. 4I is a laser confocal image of the Ik-2 transgenic at 15 hpf with nearly total failure of c-MYB expression.
Figure 4G:
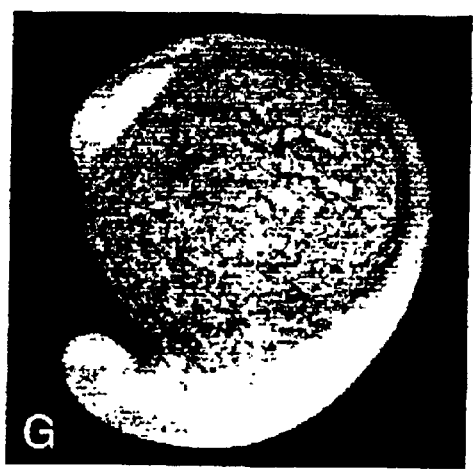
FIG. 4G is a laser confocal image of the control embryo at 15 hpf showing fluorescent c-MYB positive strip.

In all control embryos tested with human Ikaros and ZF c-MYB riboprobes at 15 hpf, c-MYB-positive cells were condensed in the distinct region of the ICM (FIG. 4G). Similar to GATA-1, the region of c-MYB positive cells was visibly enlarged in the Ik-4 transgenic ZF embryos (FIG. 4H), and dramatically decreased in the Ik-2 transgenic embryos with expression restricted to the uttermost caudal portion of the ICM (FIG. 4I).

Figure 4J:
FIG. 4J is a lateral view of the control 4 dpf ZF larvae with Rag-1 positive cells localized to the area of pharangyl arches between the eye and pectorial fin.
Figure 4H:
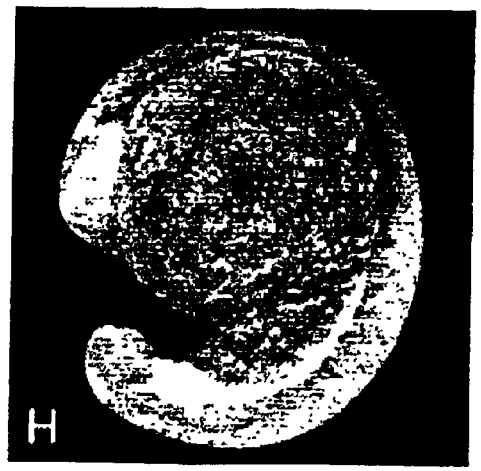
FIG. 4H is a laser confocal image of the Ik-4 transgenic embryo at 15 hpf showing an expansion of the c-MYB positive cells in the cotal part of the ICM.
Figure 4K:
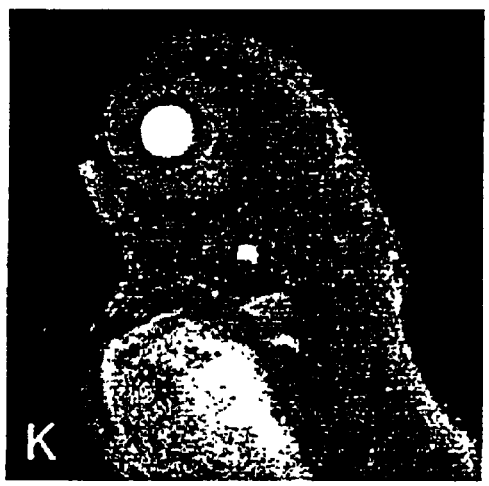
FIG. 4K is a lateral view of the Ik-4 injected larvae at 4 dpf with Rag-1 positive thymic site.
Figure 4L:
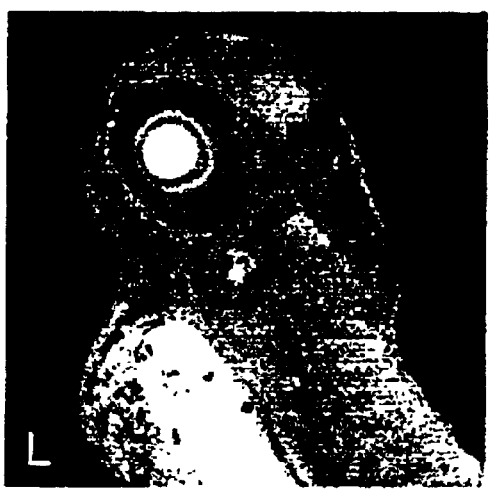
FIG. 4L is a lateral view of the Ik-2 injected larvae at 4 dpf with Rag-1 positive thymic site.
Figure 4M:
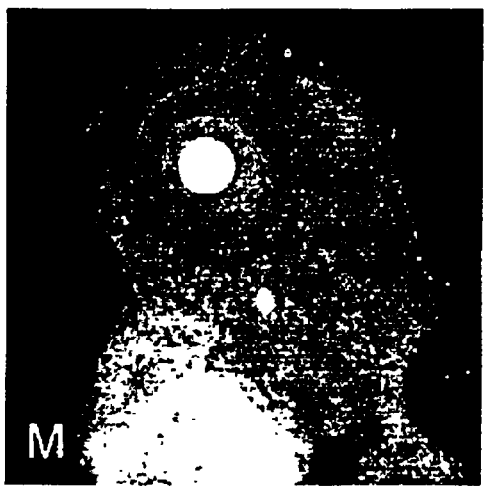
FIG. 4M is a control non-injected ZF larvae at 4 dpf with lck positive thymic site.
Figure 4N:
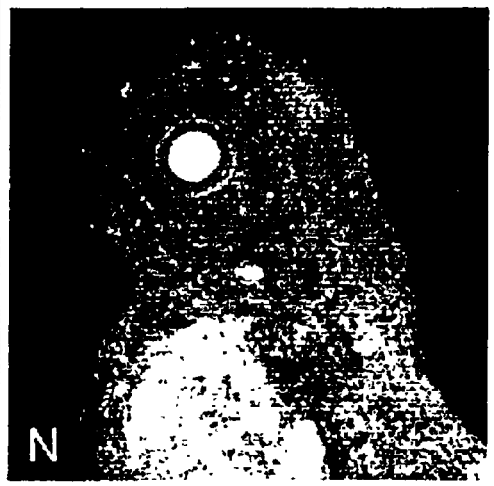
FIG. 4N shows an Ik-4 injected ZF larvae at 4 dpf with lck positive thymic site.
Figure 4O:
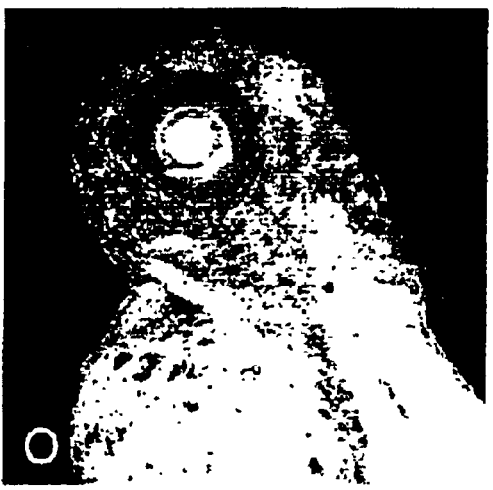

In contrast, expression of Rag-1 was not altered in the Ik-4 nor in the Ik-2 transgenic embryos. In all embryos, positive fluorescent signals which mark Rag-1 expression were restricted at 4 dpf to the bi-lateral sites of developing thymus, and were localized to the region of pharyngeal arches between the eye and pectoral fin (FIGS. 4J, 4J, 4L). Similar to Rag-1, the ZF lck expression in the control non-injected ZF larvae at 4–5 dpf was restricted to the thymic location (FIG. 4M). The lck expression was not affected in the Ik-4 injected larvae (FIG. 4N) but was dramatically decreased or totally absent in the Ik-2 injected ZF larvae at 4–5 dpf (FIG. 4O).

Example 5

Abnormal Hematopoiesis with Lymphoid Hyperplasia in Adult ZF Derived from Ikaros 4 Transgenic Embryos Adult fish derived from the Ik-4 and Ik-2 transgenic embryos as well as from non-injected control embryos were raised in similar conditions as 3 separate groups. At 3 months of age, these fish were all in apparent good health with normal shape and coloration, and reached maturity according to the breeding behavior and pair-wise mating. The body weight, body length, liver size and spleen size of Ik-4 and Ik-2 injected ZF were not different from those of the adult non-transgenic control fish (Table 2).

TABLE 2

Analysis of Adult Fish

|  | n | Mean (± SEM) | Median | Range | p-value | Difference |
|---|---|---|---|---|---|---|
| Length |  |  |  |  |  |  |
| Ik-4 | 18 | 3.74 ± 0.07 | 3.8 | 3.15–4.10 | 0.48 | NO |
| Ik-2 | 22 | 3.53 ± 0.05 | 3.5 | 3.0–4.0 | 0.18 | NO |
| intact control | 8 | 3.76 ± 0.22 | 3.95 | 2.75–4.5 |  |  |
| Weight |  |  |  |  |  |  |
| Ik-4 | 18 | 491.71 ± 32.4 | 531.25 | 274.92–704.29 | 0.28 | NO |
| Ik-2 | 22 | 416.87 ± 30.32 | 367.49 | 272.28–862.7 | 0.28 | NO |
| intact control | 8 | 454.19 ± 52.59 | 482.52 | 181.68–651.39 |  |  |
| Liver/total wt |  |  |  |  |  |  |
| Ik-4 | 18 | 2.36 ± 0.32 | 1.57 | 1–4.98 | 0.29 | NO |
| Ik-2 | 22 | 2.06 ± 0.32 | 1.57 | 0.65–6.56 | 0.43 | NO |
| intact control | 8 | 2.13 ± 0.27 | 2.25 | 0.89–3.1 |  |  |
| Spleen/total wt |  |  |  |  |  |  |
| Ik-4 | 17 | 0.08 ± 0.01 | 0.08 | 0.03–0.17 | 0.35 | NO |
| Ik-2 | 19 | 0.11 ± 0.01 | 0.11 | 0.03–0.21 | 0.15 | NO |
| intact control | 6 | 0.09 ± 0.02 | 0.1 | 0.04–0.13 |  |  |

In adult ZF, kidney plays the role of the bone marrow in mammals. Kidney hematopoietic cells from 50 mature 3-month-old adult ZF derived from the Ik-4 transgenic, Ik-2 transgenic, and intact embryos were imprinted onto slides and differentially stained with Wright/Giemsa for microscopic examination of cellularity and cellular composition. Hematopoietic cell indexes were calculated for 18 adult ZF derived from the Ik-4 injected embryos, 22 adult ZF derived from the Ik-2 injected embryos, and 10 adult ZF derived from the control non-injected embryos.

Figure 5A:
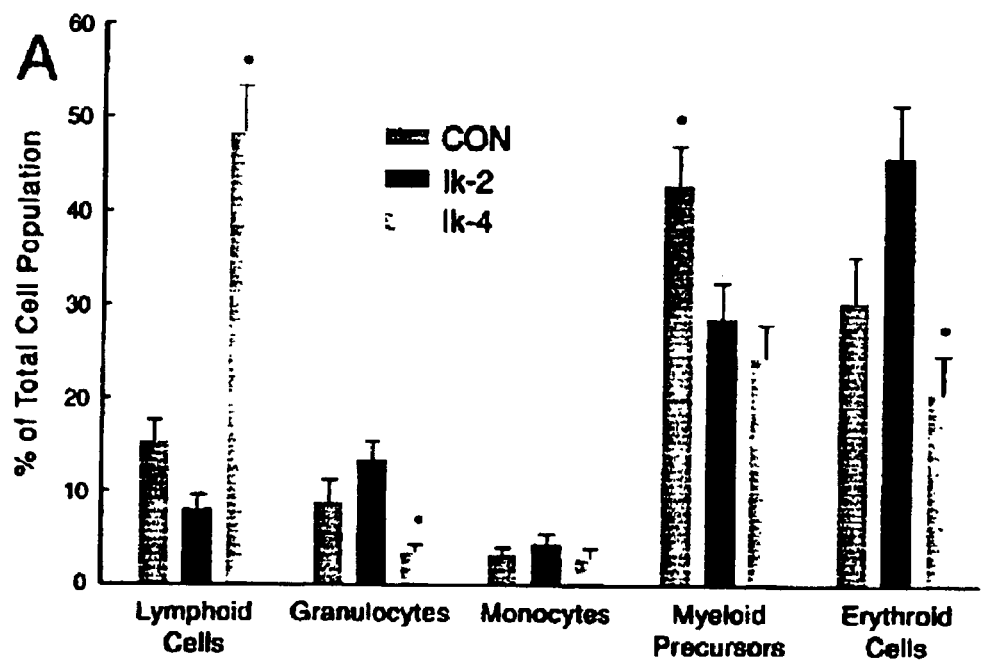
FIG. 5A is a graphic representation of hematopoietic cell indexes calculated for adult ZF derived from Ik-4 injected embryos (n=18), adult ZF derived from Ik-2 injected embryos (n=22), and adult ZF derived from control non-injected embryos (n=10).

To examine representation of hematopoietic cell types in adult fish, kidneys extracted from 18 Ik-4 injected, 22 Ik-2 injected and 10 non-injected adult ZF were imprinted on slides and stained differentially with Wright/Giemsa. All samples contained a multilineage population of hematopoietic cells including both progenitors and mature forms (Table 2, FIG. 5A).

Figure 5B:

Imprints from the control, non-injected ZF showed multilineage hematopoiesis with marked myeloid (43%) and erythroid (30%) hyperplasia. Other cell types identified in the imprints consisted of lymphoid cells (15%), granulocytes (10%) and monocytes (5%) (Table 2, FIGS. 5A–5B). In contrast, in the ZF derived from the Ik-4 injected embryos, lymphoid cells represented 49% of hematopoietic cell population, whereas myeloid and erythroid cells as well as granulocytes were reduced in numbers (24%, 21%, and 3%, respectively), and the number of monocytes remained unchanged (3%) (Table 2, FIGS. 5A & 5D). In the ZF derived from the Ik-2 injected embryos, the number of erythroid cells was drastically increased (46%), while cells of the myeloid and lymphoid lineages were present in reduced numbers (29% and 8%, respect vely). The number of granulocytes was slightly increased (13%), and the number of monocytes was not markedly changed (4%) (Table 2, FIGS. 5A & 5C).

The data described herein provides evidence that the human leukemogenic dominant-negative isoform Ik-4 and human DNA-binding isoform Ik-2 are transiently expressed in ZF embryos during primitive and "fetal" definitive hematopoiesis. Early ZF hematopoietic transcription factors GATA-1 and c-MYB are affected by Ik-4 and Ik-2 expression in opposite ways; they are upregulated by Ik-4 and downregulated by Ik-2 expression.

In adult kidney, distinct lymphoproliferative disorder was observed in ZF derived from the Ik-4 transgenic embryos, and erythroproliferative disorder was detected in ZF derived from the Ik-2 transgenic embryos. The observed phenomenon can be described as a hyperplasia of specific blood cell types which occurs at the expense of other cell lineages as a late response to the Ik-4 and Ik-2 transgene expression during embryonic hematopoiesis. Accordingly, the data supports the transgenic ZF as a useful experimental model to study leukemogenesis, Lymphoproliferative disorders (e.g. leukemias) and erythroproliferative disorders (e.g. anemia).

Discussion

All vertebrates including mammals and fish, utilize the same basic principles and share the same major steps of blood development, with waves of primitive and definitive hematopoiesis, successive changes of hematopoietic sites in ontogeny, and colonization of hemopoietic organs by blood cell precursors of specific lineages. In this respect, the ZF provides an excellent model to define genes and genetic pathways essential for blood cell differentiation and development of hematopoietic disorders.

In several large-scale chemical mutagenesis screens, over 50 mutations were identified in the ZF which affect differentiation in red cell (Ransom et al., 1996, Weinstein et al., 1996) and white cell lineages (Trede and Zon, 1998, Dr. Nikolaus Trede, personal communication). It has been shown recently that disruption of the sau gene, which leads to microcytic hypochromic anemia phenotype in ZF corresponds to impaired gene coding for erythroid-specific d-aminolevulinate synthase (ALAS2/ALAS-E) necessary for heme biosynthesis, and results in congenital sideroblastic anemia in humans (Brownlie et al., 1998). Mutation of another gene, $yqe^{tp61}$, leads in the ZF to a photosensitive porphyria. This was linked to uroporphyrinogen decarboxylase (UROD)-deficiency which causes hepatoerythropietic porphyria in humans (Wang et al., 1998). A spontaneous blood mutation, cloche (clo), was found to affect both blood and endothelial cell differentiation in ZF (Stainier et al., 1995), most probably by disrupting normal SCL (Tal-1) expression in hemangioblasts (Liao et al., 1998, Gering et al., 1998). These findings demonstrate that at least some ZF blood mutations serve as models for human blood disorders.

In support of the ZF as a model animal, it is noted that feasible and reliable vehicles necessary for either transient transgene expression or stable integration and expression are well developed for the ZF. In addition, the data recited herein demonstrates that two isoforms of the human Ikaros gene that play a critical role in lymphocyte differentiation were expressed in the ZF during embryonic hematopoiesis. Transgene expression was regulated in the ZF cells, for it started after the onset of the zygotic genome transcription. It persisted for the first two days in 100% of the injected embryos and in approximately 50% and 40% of the 3 dpf embryos and 4 dpf larvae, respectively.

The β-actin promoter, cloned into the all-fish expression cassette have used herein was intended to drive transgene expression in all types of fish cells. Expression was detected in a variety of cells including mesenchyme cells of dorsal aorta ventral wall and ventral vein region as well as in circulating blood cells. Thus, transgene activity in the appropriate cells with appropriate micro-environment may be the cause of future hematopoietic alteration.

A layout of blood development in the ZF embryo served as a necessary background for the present study. In the ZF, the first cells committed to blood differentiation were defined as early as the end of gastrulation as two lateral stripes of ventral mesoderm with cells (hemangioblasts) expressing, as shown by in situ hybridization, early hematopoietic and vasculogenic markers SCL, GATA-1, GATA-2, c-MYB and LMO2 (Detrich et al., 1995, Gering et al., 1998, Liao et al., 1998, Thompson et al., 1998, Amatruda and Zon, 1999). These cells migrate to somite mesoderm to form in about 2 hours (the 5 somite stage) the intermediate cell mass (ICM). The ICM is known to be the site of primitive hematopoiesis in fish (Al-Adhami and Kunz, 1977, Detrich et al., 1995; Willett et al., 1999) and comprises hematopoietic (primarily embryonic erythroblasts), vasculogenic cells as well as pronephric cell precursors (Zon, 1995, Weinstein et al., 1996, Liao et al., 1998, Thompson et al., 1998, Willett et al., 1999). The ICM declines with the production of circulating erythroblasts and erythrocytes and by 30 hpf hematopoiesis shifts to the nascent "dorsal" site possibly the first sites of definitive hematopoiesis, the dorsal aorta and to the "ventral vein region" containing blood cell precursors in the axial vein walls and surrounding mesenchyme (Liao et al., 1998, Thompson et al., 1998, Willett et al., 1999). From here two separate seedings take place: of thymus (at 65 hpf) and of kidney primordia (starting at 96 hpf) (Hansen and Zapata, 1998, Trede and Zon, 1998, Willett et al., 1999). While thymus is colonized by T-lymphocyte precursors, pronephros is seeded with different lineage progenitors including erythro-, myelo- and B-lymphocytes. Finally, with kidney differentiation into head kidney (pronephros) and trunk kidney (mesonephros), the main multilineage hematopoietic site in adults is formed which is unequivocally considered to be a bone marrow equivalent (Rowley et al., 1988, Hansen and Zapata, 1998).

Interaction of the Human Ikaros Isoforms with the ZF Hematopoietic Genes.

The data presented herein shows that the area of ZF GATA-1 expression in the Ik-4-positive embryos at 17 hpf was markedly increased than in the control and Ik-4 negative embryos. Taking into consideration that GATA-1 is the earliest marker to be expressed in blood cell progenitors, this shift in GATA-1 expression pattern suggests enlargement of the whole ICM region in the embryo. The effect of the Ik-2 transgene was totally opposite—the GATA-1 positive ICM area was drastically reduced. Similarly, human Ikaros isoforms affected expression of the ZF c-MYB. In the Ik-4 transgenic embryos at 15 hpf, c-MYB-positive area in the ICM was enlarged whereas in the Ik-2 transgenic embryos, the strip of c-MYB-positive cells was mostly missing showing a decline in c-MYB expression. Finally, in Ik-2 injected ZF larvae at 4 and 5 dpf, lck expression in thymocytes was visibly reduced or totally blocked. It should be noted tha in ZF embryos, expression of ZF Ikaros gene was detected by in situ hybridization in the ICM (at 5 somite stage and at 24 hpf) and then in the dorsal aorta at 46 hpf (Kawasaki et al., 1998). Thus, in addition to a role in determination of hematopoietic stem cell commitment to lymphoid lineage in adults (Hansen et al., 1997), Ikaros marks in the ZF embryo, the earliest hematopoietic lymphoid progenitors.

In humans and fish (trout), Ikaros was found to be highly conserved showing 75% homology in amino acid sequence and 92–98% identity in the active sites of the protein (Hansen et al., 1997). Structural similarity gives grounds to assume that both human Ikaros isoforms can interact with endogenous ZF Ikaros, as well as with other ZF genes involved in blood cell differentiation. Overexpression of DNA-binding Ikaros isoform in the blood cell progenitors as well as the occurrence of the non-binding isoform equally affects blood development.

Distribution of Transgene Expression.

Ik-4 and Ik-2 transgenes were expressed in the ZF embryos in a mosaic fashion. As evidenced by whole-mount in situ hybridization, human Ikaros RNA resided in various regions of the embryo but most commonly in the trunk area, in close proximity to the ICM site. Transgene expression was confirmed by immunostaining and human Ikaros isoforms were localized in the 48 embryos to a number of hematopoietic and nonhematopoietic cells. Along with the sites of ectopic expression, the trunk region of the embryo which at this stage contains the dorsal aorta and axial vein complex was commonly found positive also.

Human Ik-4 isoform was detected in the circulating blood cells, as well as in the hematopoietic cells of dorsal aorta ventral wall and cells surrounding the caudal portion of the axial vein, known as a ventral hematopoietic site (Liao et al., 1998). Human Ik-2 isoform was detected in circulating blood cells as well as in endothelial cells of the axial vessels. Large hematopoietic cells of the "dorsal" site as well as similar large cells in the blood stream retained Ik-4 protein in the nucleus and in the cytoplasm, whereas the smaller and much more round cells of primitive blood retained no signal in the nucleus supposedly due to its inactivation. Ik-2 protein was localized to the nucleus and to the cytoplasm of the circulating blood cells.

The data show that human Ikaros gene expression in the transgenic ZF embryo may be both ectopic and site-specific. While in non-hematopoietic cells Ik-4 and Ik-2 transgene activity is probably irrelevant to blood development, their action in the ICM and the "dorsal" sites of embryonic hematopoiesis may cause significant changes in the pattern of endogenous ZF Ikaros expression with dramatic consequences for blood cell differentiation. The observed changes in the GATA-1, c-MYB, and lck expression patterns suggest that directly or indirectly the activity of these early blood cell markers was affected by the transgenes.

To avoid ectopic expression, transgenes may be targeted to specific cell types. Recent study of the ZF GATA-1 promoter showed that positive and negative cis-regulatory elements are essential for erythroid-specific expression (Meng et al., 1999). Promoters from lymphoid-specific ZF genes (Rag 1,2, lck, Ikaros) can be used to force transgene expression exclusively in one of the cell lineages. By choosing a cell-specific gene promoter, transgene activation can be restricted to desired cell types.

Primitive Blood Circulation.

It was generally accepted that embryonic erythrocytes form the only population of circulating blood cells in the 24–48 hpf ZF embryos. However, large non-erythroid cells defined as granulocytes according to their ultrastructure, were found in the blood stream of the 48 hpf ZF embryos (Lieschke et al., 1999). This finding make it possible to assume that other types of blood cells, including lymphoid progenitors may be present in circulating blood in the ZF embryo. The data presented herein shows that in the 48 hpf transgenic ZF embryos, both Ik-4 and Ik-2 human Ikaros isoforms reside in the nuclei and cytoplasm of large non-differentiated cells found in circulation, as well as in the non-differentiated cells of the dorsal aorta ventral wall and ventral vein mesenchyme cells. These cells, affected by either dominant-negative Ik 4 expression or by overexpression of the DNA-binding Ik-2 isoform, may comprise the cell pool which seeds the kidney primordium, and thus, be responsible for future changes in adult hematopoiesis.

Blood Cell Types in Adult Fish.

Hematopoietic tissue in the ZF kidney is formed by cords of cells which surround blood vessels, in-between the renal tubules and glomeruli (Willett et al., 1999). Erythrocyte, granulocyte, lymphocyte, and monocyte differentiation has been reported in the adult fish kidney (Rowley et al., 1988) and with the exception of nucleated erythrocytes, the morphology of the other mature and differentiating hematopoietic cells closely resembles that of their mammalian counterparts. Morphological description of fish blood cells, including their ultrastructure and functions is summarized in Rowley et al., 1988.

There are two subpopulations of lymphocytes in fish with different immunological properties as reviewed by Miller et al., 1998, which precisely correspond to T- and B-cells. T-lymphocytes are located predominantly in thymus where Ikaros (Hansen and Zapata, 1998), Rag 1,2, and lck, a src-family protein tyrosine kinase implicated in T-cell maturation and activation (Trede and Zon, 1998) are expressed. B-lymphocytes are generated in the kidney; in trout and ZF, Ikaros (Hansen et al., 1997), Rag-1 and Rag-2 (Willett et al., 1997) and TdT (Hansen, 1997) expression in the pronephros was used to confirm the presence of pre-B-cells. A tec-family non-receptor tyrosine kinase expression was found recently in the ZF kidney (Haire et al., 1998) which may represent the Btk expression in the B-lymphocytes.

Neoplasia in Fish.

For several reasons, neoplastic transformation in fish is not widely reported in the literature. Nonetheless, fish are susceptible to neoplasms and as models were successfully utilized in the studies of carcinogenic and teratogenic effects of aquatic pollutants (Pliss et al., 1982, Mizell and Romig, 1997, Oberemm, 2000). In this respect, fish are especially noted for experimentally-induced neoplastic responses in liver reviewed by Hinton and Couch, 1998). Besides hepatocarcinomas, such as in tilapia (Ding et al., 1989), there were reported cases of olfactory neuroepithelioma in domestic carp (Ishikawa et al., 1978) and abdominal sarcoma in koi carp (Lewbart et al., 1998), plasmacytoid leukemia of a retroviral origin in chinook salmon (Kent et al., 1997) and lymphosarcoma of unknown origin in brook trout (Earnest-Koons et al., 1997). Quite separately stands a very elaborate study of malignant melanomas in platyfish caused by a dominant oncogene ONC-Xmark which is a thyrosine kinase receptor gene (Schartl et al., 1985). A model for melanogenesis and tumor formation in fish in particular, was proposed (Morizot et al., 1998). Accordingly, the literature supports the study cancerogenesis in small fish model systems, such as ZF. Recently, ZF was proposed as a model for human blood disorders such as congenital sideroblastic anemia and hepatoerythropoietic porphyria (Brownlie et al., 1998), (Wang et al., 1998). The data presented herein indicates that the ZF may serve as an experimental model of leukemia development as well.

Figure 3B:
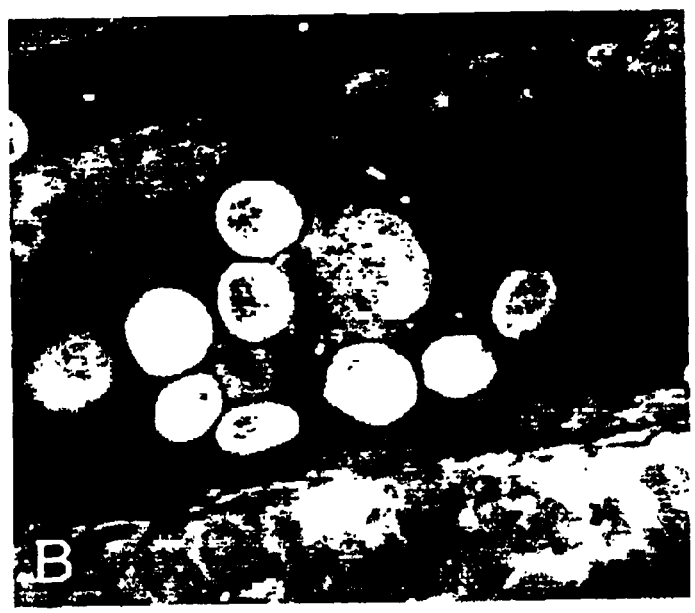
FIGS. 3B–3E show frozen sagittal sections of the embryo immunostained with antibodies raised against human Ikaros.
Figure 3C:
Figure 3D:
Figure 3E:

FIGS. 3A–3B demonstrate this pheonotypic change. FIG. 3A shows a normally pigmented larva, while FIG. 3B shows a larva with a/oligochromemia. Primitive circulating erythrocytes extracted from the fry with a/oligichromemia were indistinguishable in size and shape from the normal ones, and the loss of pigmentation was the only alteration of blood cell phenotype observed in these fish. Fry with oligochromemia were found viable and were raised and further analyzed separately from the others.

Example 6

Screening Potential Candidate Drugs for Therapeutically Effective Agent

The animal model of the invention can be used to screen candidate compounds for therapeutic utility in the treatment and/or prevention of lymphatopoietic and hemapoietic disorders, including leukemias. As discussed in the examples above, the insertion of the transgene IK4 into zebrafish embryos markedly altered the normal cellular differentiation pattern and is correleated with the development of hematopoietic disorders, including multilineage hematopoiesis, erythroid hyperplasia, and the like.

Administration of a putative therapeutic agent to the animal model provides an efficient, cost-effective, and reliable method for screeing agents for candidates likely to improve outcome and symptoms of hematopoietic disorders, including leukemias.

Example 7

Screening Potential Carcinogens

The animal model for the invention can be used to screen suspected carcinogenic agents, or agents suspected of inducing lymphatopoietic or hepatapoietic disorders. For example, ZF embryos expressing the Ik-2 transgenes produce and develop normal B- and T-lineage cells. Agents that might disrupt normal Ik-2 or other regulating controls for normal hematopoietic cell development can be efficiently and rapidly screened by administering the suspected agent to the embryo, as demonstrated by administration of Ik-4 in the Examples above.

References

Al-Adhami, M. A., and Kunz, Y. W. (1977). Ontogenesis of Haematopoietic Sites in Rrachydanio rerio (Hamilton-Buchanan) (Teleostei). Develop., Growth and Differ. 19, #2, 171–179.

Amatruda, J. F., and Zon, L. I. (1999). Dissecting hematopoiesis and disease using the zebrafish. Dev Biol 216, 1–15.

Amemiya, C. T. (1998). The zebrafish and haematopoietic justice [news; comment]. Nat Genet 20, 222–3.

Bahary, N., and Zon, L. I. (1998). Use of the zebrafish (Danio rerio) to define hematopoiesis. Stem Cells 16, 89–98.

Brown, K. E., Guest, S. S., Smale, S. T., Hahm, K., Merkenschlager, M., and Fisher, A. G. (1997). Association of transcriptionally silent genes with Ikaros complexes at centromeric heterochromatin. Cell 91, 845–54.

Brownlie, A., Donovan, A., Pratt, S. J., Paw, B. H., Oates, A. C., Brugnara, C., Witkowska, H. E., Sassa, S., and Zon, L. I. (1998). Positional cloning of the zebrafish sauternes gene: a model for congenital sideroblastic anaemia [see comments]. Nat Genet 20, 244–50.

Caldovic, L., and Hackett, P. B., Jr. (1995). Development of position-independent expression vectors and their transfer into transgenic fish. Mol Mar Biol Biotechnol 4, 51–61.

Crist, W. M., Shuster, J. J., Falletta, J., Pullen, D. J., Berard, C. W., Vietti, T. J., Alvarado, C. S., Roper, M. A., Prasthofer, E., and Grossi, C. E. (1988). Clinical features and outcome in childhood T-cell leukemia-lymphoma according to stage of thymocyte differentiation: a Pediatric Oncology Group Study. Blood 72, 1891–7.

Culp, P., Nusslein-Volhard, C., and Hopkins, N. (1991). High-frequency germ-line transmission of plasmid DNA sequences injected into fertilized zebrafish eggs. Proc Natl Acad Sci U S A 88, 7953–7.

Detrich, H. W., 3rd, Kieran, M. W., Chan, F. Y., Barone, L. M., Yee, K., Rundstadler, J. A., Pratt, S., Ransom, D., and Zon, L. I. (1995). Intraembryonic hematopoietic cell migration during vertebrate development. Proc Natl Acad Sci U S A 92, 10713–7.

Ding, J. L., Hee, P. L., and Lam, T. J. (1989). Differential susceptibility of a fish, tilapia Oreochromis mossambicus (Teleostei, Cichlidae) to hepatocarcinogenesis by diethylnitrosamine and methylazoxymethanol acetate. Carcinogenesis 10, 493–9.

Driever, W., and Fishman, M. C. (1996). The zebrafish: heritable disorders in transparent embryos. J Clin Invest 97, 1788–94.

Earnest-Koons, K. A., Schachte, J. H., Jr., and Bowser, P. R. (1997). Lymphosarcoma in a brook trout. J Wildl Dis 33, 666–9.

Ford, A. M., Ridge, S. A., Cabrera, M. E., Mahmoud, H., Steel, C. M., Chan, L. C., and Greaves, M. (1993). In utero rearrangements in the trithorax-related oncogene in infant leukaemias. Nature 363, 358–60.

Georgopoulos, K., Bigby, M., Wang, J. H., Molnar, A., Wu, P., Winandy, S., and Sharpe, A. (1994). The Ikaros gene is required for the development of all lymphoid lineages. Cell 79, 143–56.

Georgopoulos, K., Moore, D. D., and Derfler, B. (1992). Ikaros, an early lymphoid-specific transcription factor and a putative mediator for T cell commitment. Science 258, 808–12.

Georgopoulos, K., Winandy, S., and Avitahl, N. (1997). The role of the Ikaros gene in lymphocyte development and homeostasis. Annu Rev Immunol 15, 155–76.

Gering, M., Rodaway, A. R., Gottgens, B., Patient, R. K., and Green, A. R. (1998). The SCL gene specifies haemangioblast development from early mesoderm. Embo J 17, 4029–45.

Gill Super, H. J., Rothberg, P. G., Kobayashi, H., Freeman, A. I., Diaz, M. O., and Rowley, J. D. (1994). Clonal, nonconstitutional rearrangements of the MLL gene in infant twins with acute lymphoblastic leukemia: in utero chromosome rearrangement of 11q23. Blood 83, 641–4.

Greaves, M. F. (1986). Differentiation-linked leukemogenesis in lymphocytes. Science 234, 697–704.

Hahm, K., Ernst, P., Lo, K., Kim, G. S., Turck, C., and Smale, S. T. (1994). The lymphoid transcription factor LyF-1 is encoded by specific, alternatively spliced mRNAs derived from the Ikaros gene. Mol Cell Biol 14, 7111–23.

Haire, R. N., Strong, S. J., and Litman, G. W. (1998). Tec-family non-receptor tyrosine kinase expressed in zebrafish kidney. Immunogenetics 47, 336–7.

Hammerschmidt, M., Blader, P., and Strahle, U. (1999). Strategies to perturb zebrafish development. Methods Cell Biol 59, 87–115.

Hansen, J. D. (1997). Characterization of rainbow trout terminal deoxynucleotidyl transferase structure and expression. TdT and RAG1 co-expression define the trout primary lymphoid tissues. Immunogenetics 46, 367–75.

Hansen, J. D., Strassburger, P., and Du Pasquier, L. (1997). Conservation of a master hematopoietic switch gene during vertebrate evolution: isolation and characterization of Ikaros from teleost and amphibian species. Eur J Immunol 27, 3049–58.

Hansen, J. D., and Zapata, A. G. (1998). Lymphocyte development in fish and amphibians. Immunol Rev 166, 199–220.

Hinton, D. E., and Couch, J. A. (1998). Architectural pattern, tissue and cellular morphology in livers of fishes: relationship to experimentally-induced neoplastic responses. Exs 86, 141–64.

Hyatt, T. M., and Ekker, S. C. (1999). Vectors and techniques for ectopic gene expression in zebrafish. Methods Cell Biol 59, 117–26.

Ishikawa, T., Masahito, P., and Takayama, S. (1978). Olfactory neuroepithelioma in a domestic carp (Cyprinus carpio). Cancer Res 38, 3954-9.

Jowett, T. (1999). Analysis of protein and gene expression. Methods Cell Biol 59, 63–85.

Kawasaki, H., Trede, N. S., Rast, J. P., Ota, T., Halevi, A., Pratt, S. J., Postlewait, J. H., Litman, G. W., Zon, L. I., and Amemiya, C. T. (1998). Zebrafish Ikaros gene is necessary for differentiation of the immune system. In American Society of Hematology, 40th Annual Meeting (Miami Beach, Fla., pp. 575a.

Kent, M. L., Eaton, W. D., and Casey, J. W. (1997). Plasmacytoid leukemia of chinook salmon. Leukemia 11 Suppl 3, 170–1.

Klug, C. A., Morrison, S. J., Masek, M., Hahm, K., Smale, S. T., and Weissman, I. L. (1998). Hematopoietic stem cells and lymphoid progenitors express different Ikaros isoforms, and Ikaros is localized to heterochromatin in immature lymphocytes. Proc Natl Acad Sci U S A 95, 657–62.

Lewbart, G. A., Spodnick, G., Barlow, N., Love, N. E., Geoly, F., and Bakal, R. S. (1998). Surgical removal of an undifferentiated abdominal sarcoma from a koi carp (Cyprinus carpio). Vet Rec 143, 556–8.

Liao, E. C., Paw, B. H., Oates, A. C., Pratt, S. J., Postlethwait, J. H., and Zon, L. I. (1998). SCL/Tal-1 transcription factor acts downstream of cloche to specify hematopoietic and vascular progenitors in zebrafish. Genes Dev 12, 621–6.

Lieschke, G. J., Oates, A. C., Paw, B. H., Ho, R. K., Zon, L. I., and Layton, J. E. (1999). pu. 1 marks an anteriolateral site of myeloid commitment in the postgastrulation zebrafish embryo independent of ventral erythroid-determining signals. In American Society of Hematology, 41 st Annual Meeting (New Orleans, La., pp. 651a.

Luna, L. G. (1968). Manual of histologic staining methods of the Armed Forces Institute of pathology: McGraw-Hill Book Company, pp. 258.

Meng, A., Tang, H., Yuan, B., Ong, B. A., Long, Q., and Lin, S. (1999). Positive and negative cis-acting elements are required for hematopoietic expression of zebrafish GATA-1. Blood 93, 500–8.

Miller, N., Wilson, M., Bengten, E., Stuge, T., Warr, G., and Clem, W. (1998). Functional and molecular characterization of teleost leukocytes. Immunol Rev 166, 187–97.

Mizell, M., and Romig, E. S. (1997). The aquatic vertebrate embryo as a sentinel for toxins: zebrafish embryo dechorionation and perivitelline space microinjection. Int J Dev Biol 41, 411–23.

Molnar, A., and Georgopoulos, K. (1994). The Ikaros gene encodes a family of functionally diverse zinc finger DNA-binding proteins. Mol Cell Biol 14, 8292–303.

Molnar, A., Wu, P., Largespada, D. A., Vortkamp, A., Scherer, S., Copeland, N. G., Jenkins, N. A., Bruns, G., and Georgopoulos, K. (1996). The Ikaros gene encodes a family of lymphocyte-restricted zinc finger DNA binding proteins, highly conserved in human and mouse. J Immunol 156, 585–92.

Morizot, D. C., McEntire, B. B., Della Coletta, L., Kazianis, S., Schartl, M., and Nairn, R. S. (1998). Mapping of tyrosine kinase gene family members in a Xiphophorus melanoma model. Mol Carcinog 22, 150–7.

Nguyen, V. H., Schmid, B., Trout, J., Connors, S. A., Ekker, M., and Mullins, M. C. (1998). Ventral and lateral regions of the zebrafish gastrula, including the neural crest progenitors, are established by a bmp2b/swirl pathway of genes. Dev Biol 199, 93–110.

Nusslein-Volhard, C. (1994). Of flies and fishes. Science 266, 572–4.

Oberemm, A. (2000). The use of a refined zebrafish embryo bioassay for the assessment of aquatic toxicology. Lab Animals 29, 32–40.

Orkin, S. H., and Zon, L. I. (1997). Genetics of erythropoiesis: induced mutations in mice and zebrafish. Annu Rev Genet 31, 33–60.

Pizzo, P., and Poplack, D., [eds]. (1993). Acute Lymphoblastic Leukemia. Principles and Practice of Pediatric Oncology, 2nd Ed Edition: J. P. Lippincott Company).

Pliss, G. B., Zabezhinski, M. A., Petrov, A. S., and Khudoley, V. V. (1982). Peculiarities of N-nitramines carcinogenic action. Arch Geschwulstforsch 52, 629–34.

Ransom, D. G., Haffter, P., Odenthal, J., Brownlie, A., Vogelsang, E., Kelsh, R. N., Brand, M., van Eeden, F. J., Furutani-Seiki, M., Granato, M., Hammerschmidt, M., Heisenberg, C. P., Jiang, Y. J., Kane, D. A., Mullins, M. C., and Nusslein-Volhard, C. (1996). Characterization of zebrafish mutants with defects in embryonic hematopoiesis. Development 123, 311–9.

Rowley, A. F., Hunt, T. C., Page, M., and Mainwaring, G. (1988). Vertebrate blood cells, R. A. F. and N. A. Ratcliffe, eds.: Cambridge University Press).

Schartl, M., Schmidt, C. R., Anders, A., and Barnekow, A. (1985). Elevated expression of the cellular src gene in tumors of differing etiologies in Xiphophorus. Int J Cancer 36, 199–207.

Stainier, D. Y., Weinstein, B. M., Detrich, H. W., 3rd, Zon, L. I., and Fishman, M. C. (1995). Cloche, an early acting zebrafish gene, is required by both the endothelial and hematopoietic lineages. Development 121, 3141–50.

Stuart, G. W., Vielkind, J. R., McMurray, J. V., and Westerfield, M. (1990). Stable lines of transgenic zebrafish exhibit reproducible patterns of transgene expression. Development 109, 577–84.

Sun, L., Heerema, N., Crotty, L., Wu, X., Navara, C., Vassilev, A., Sensel, M., Reaman, G. H., and Uckun, F. M. (1999). Expression of dominant-negative and mutant isoforms of the antileukemic transcription factor Ikaros in infant acute lymphoblastic leukemia. Proc Natl Acad Sci U S A 96, 680–685.

Sun, L., Liu, A., and Georgopoulos, K. (1996). Zinc finger-mediated protein interactions modulate Ikaros activity, a molecular control of lymphocyte development. Embo J 15, 5358–69.

Thompson, M. A., Ransom, D. G., Pratt, S. J., MacLennan, H., Kieran, M. W., Detrich, H. W., 3rd, Vail, B., Huber, T. L., Paw, B., Brownlie, A. J., Oates, A. C., Fritz, A., Gates, M. A., Amores, A., Bahary, N., Talbot, W. S., Her, H., Beier, D. R., Postlethwait, J. H., and Zon, L. I. (1998). The cloche and spadetail genes differentially affect hematopoiesis and vasculogenesis. Dev Biol 197, 248–69.

Trede, N. S., and Zon, L. I. (1998). Development of T-cells during fish embryogenesis. Dev Comp Immunol 22, 253–63.

Uckun, F. M., Sensel, M. G., Sun, L., Steinherz, P. G., Trigg, M. E., Heerema, N. A., Sather, H. N., Reaman, G. H., and Gaynon, P. S. (1998). Biology and treatment of childhood T-lineage acute lymphoblastic leukemia. Blood 91, 735–46.

Wang, H., Long, Q., Marty, S. D., Sassa, S., and Lin, S. (1998). A zebrafish model for hepatoerythropoietic porphyria [see comments]. Nat Genet 20, 239–43.

Wang, J. H., Nichogiannopoulou, A., Wu, L., Sun, L., Sharpe, A. H., Bigby, M., and Georgopoulos, K. (1996). Selective defects in the development of the fetal and adult lymphoid system in mice with an Ikaros null mutation. Immunity 5, 537–49.

Weinstein, B. M., Schier, A. F., Abdelilah, S., Malicki, J., Solnica-Krezel, L., Stemple, D. L., Stainier, D. Y., Zwartkruis, F., Driever, W., and Fishman, M. C. (1996). Hematopoietic mutations in the zebrafish. Development 123, 303–9.

Westerfield, M., [ed]. (1995). The Zebrafish Book, 3rd Edition: (University of Oregon Press, Eugene).

Weston, K. (1999). Reassessing the role of C-MYB in tumorigenesis. Oncogene 18, 3034–8.

Willett, C. E., Cortes, A., Zuasti, A., and Zapata, A. G. (1999). Early hematopoiesis and developing lymphoid organs in the zebrafish. Dev Dyn 214, 323–36.

Willett, C. E., Zapata, A. G., Hopkins, N., and Steiner, L. A. (1997). Expression of zebrafish rag genes during early development identifies the thymus. Dev Biol 182, 331–41.

Winandy, S., Wu, P., and Georgopoulos, K. (1995). A dominant mutation in the Ikaros gene leads to rapid development of leukemia and lymphoma. Cell 83, 289–99.

Wolff, L. (1996). Myb-induced transformation. Crit Rev Oncog 7, 245–60.

Zhang, J., Talbot, W. S., and Schier, A. F. (1998). Positional cloning identifies zebrafish one-eyed pinhead as a permissive EGF-related ligand required during gastrulation. Cell 92, 241–51.

Zon, L. I. (1995). Developmental biology of hematopoiesis. Blood 86, 2876–91.

---

We claim:

1. A zebrafish embryo comprising cells that comprise a nucleic acid molecule encoding a heterologous non-DNA binding isoform of Ikaros,
   wherein the nucleic acid molecule is transiently expressed in a hematopoietic tissue during the primitive phase of hematopoiesis, and
   wherein, when the embryo is allowed to develop into a zebrafish, the zebrafish exhibits an increased percentage of lymphoid cells in the hematopoietic lineage in comparison to a wild-type control zebrafish.

2. The zebrafish embryo of claim 1, wherein the Ikaros protein lacks at least one N-terminal zinc finger domain as compared with DNA-binding forms of Ikaros.

3. The zebrafish embryo of claim 2, wherein the Ikaros protein is one or more of Ik-4, Ik-5, Ik-6, Ik-7, and Ik-8.

4. The zebrafish embryo of claim 1, wherein the Ikaros protein is human.

5. The zebrafish embryo of claim 1, wherein the hematopoietic tissue is kidney tissue.

6. A method for screening potential therapeutic agents useful for treating lymphoid hyperplasia comprising:
   a) expressing a heterologous transiently transfected nucleic acid molecule encoding a non-DNA binding form of Ikaros in a hematopoietic tissue during primitive phase of hematopoiesis of a zebrafish embryo;
   b) contacting the zebrafish embryo of step (a) with a potential therapeutic agent;
   c) developing said zebrafish embryo into an adult zebrafish; and
   d) correlating a reduced percentage of lymphoid cells in the hematopoietic lineage in comparison to a non-contacted control with a therapeutic agent useful for treating lymphoid hyperplasia.

7. The method of claim 6, wherein the Ikaros protein lacks at least one N-terminal zinc finger domain as compared with DNA-binding forms of Ikaros.

8. The method of claim 6, wherein the Ikaros protein is one or more of Ik-4, Ik-5, Ik-6, Ik-7, and Ik-8.

9. The method of claim 6, wherein said reduced percentage of lymphoid cells comprises improved cellular composition of adult kidney imprints in comparison to that of a non-treated control zebrafish.

10. The method of claim 6, wherein the zebrafish embryos are contacted with the potential therapeutic agent prior to Ikaros expression.

11. The method of claim 6, wherein the zebrafish embryos are contacted with the potential therapeutic agent after the onset of Ikaros expression.

12. A zebrafish embryo comprising cells that comprise a nucleic acid molecule encoding a heterologous non-DNA binding isoform of Ikaros wherein the ikaros isoform is expressed in an intermediate cell mass (ICM) wherein when the embryo is allowed to develop into a zebrafish, the zebrafish exhibits lymphoid hyperplasia.

13. A zebrafish embryo comprising cells that comprise a nucleic acid molecule encoding a heterologous non-DNA binding isoform of Ikaros wherein the Ikaros isoform is expressed in a dorsal hematopoietic site wherein when the embryo is allowed to develop into a zebrafish, the zebrafish exhibits lymphoid hyperplasia.

14. The zebrafish embryo of claim 13, wherein the heterologous Ikaros protein is expressed by dorsal ventral wall mesenchyme hematopoietic cells in the dorsal hematopoietic site.

15. The zebrafish embryo of claim 13, wherein the heterologous Ikaros protein is expressed by lymphohematopoietic cells in the dorsal hematopoietic site.

16. The zebrafish embryo of claim 13, wherein the heterologous Ikaros protein is expressed by ventral vein region cells in the dorsal hematopoietic site.

17. A method for producing a zebrafish comprising introducing a heterologous nucleic acid encoding a non-DNA binding isoform of Ikaros into a zebrafish embryo wherein the nucleic acid molecule is expressed in a hematopoietic tissue during primitive phase of hematopoiesis of a zebrafish embryo, wherein the zebrafish exhibits an increased percentage of lymphoid cells in the hematopoietic lineage in comparison to a wild-type control zebrafish.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Homo sapiens

<400> SEQUENCE: 1
atggatgctg acgagggtca agac                                          24

<210> SEQ ID NO 2
<211> LENGTH: 24
<212> TYPE: DNA
<213> ORGANISM: Homo sapiens

<400> SEQUENCE: 2
ctagtggaat gtgtgctccc ctcg                                          24

<210> SEQ ID NO 3
<211> LENGTH: 24
<212> TYPE: DNA
<213> ORGANISM: Zebrafish

<400> SEQUENCE: 3
gatgatgccc ctcgtgctgt tttc                                          24

<210> SEQ ID NO 4
<211> LENGTH: 24
<212> TYPE: DNA
<213> ORGANISM: Zebrafish
```

```
<400> SEQUENCE: 4
tttctctttc ggctgtggtg gtga                                        24

<210> SEQ ID NO 5
<211> LENGTH: 10
<212> TYPE: PRT
<213> ORGANISM: Homo sapiens

<400> SEQUENCE: 5

Lys Ser Ser Met Pro Gln Lys Phe Leu Gly
1               5                   10

<210> SEQ ID NO 6
<211> LENGTH: 21
<212> TYPE: PRT
<213> ORGANISM: Homo sapiens

<400> SEQUENCE: 6

Val Thr Val Gly Ala Asp Asp Phe Arg Asp Phe His Ala Ile Ile Pro
1               5                   10                  15
Lys Ser Phe Ser Arg
            20
```